(12) United States Patent
Ghosh et al.

(10) Patent No.: US 10,617,318 B2
(45) Date of Patent: Apr. 14, 2020

(54) MAPPING ELECTRICAL ACTIVITY ON A MODEL HEART

(71) Applicant: Medtronic, Inc., Minneapolis, MN (US)

(72) Inventors: Subham Ghosh, Blaine, MN (US); Joshua J. Blauer, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 33 days.

(21) Appl. No.: 15/906,822

(22) Filed: Feb. 27, 2018

(65) Prior Publication Data
US 2019/0261876 A1 Aug. 29, 2019

(51) Int. Cl.
*A61B 5/00* (2006.01)
*A61B 5/04* (2006.01)
(Continued)

(52) U.S. Cl.
CPC ............. *A61B 5/044* (2013.01); *A61B 5/029* (2013.01); *A61B 5/02028* (2013.01); *A61B 5/04012* (2013.01); *A61B 5/0468* (2013.01); *A61B 5/0472* (2013.01); *A61B 5/04085* (2013.01); *A61B 5/1076* (2013.01); *A61B 5/1107* (2013.01); *A61B 5/7275* (2013.01); *A61B 5/743* (2013.01); *A61B 5/7475* (2013.01); *G16H 50/50* (2018.01); *A61B 5/1072* (2013.01)

(58) Field of Classification Search
CPC . A61B 5/044; A61B 5/04012; A61B 5/04085; A61B 5/0468; A61B 5/7475; G16H 50/50
See application file for complete search history.

(56) References Cited

U.S. PATENT DOCUMENTS

| 4,233,987 A | 11/1980 | Feingold |
| 4,402,323 A | 9/1983 | White |

(Continued)

FOREIGN PATENT DOCUMENTS

| CN | 1043621 A | 7/1990 |
| CN | 1253761 A | 5/2000 |

(Continued)

OTHER PUBLICATIONS

International Search Report and Written Opinion dated May 3, 2012 for International Application No. PCT/US2012/036262; 9 pages.
(Continued)

*Primary Examiner* — Sing-Wai Wu

(57) ABSTRACT

The exemplary systems and methods may be configured to monitor electrical activity from a patient using a plurality of external electrodes. The exemplary systems and methods may be further configured to provide a model heart representative of the patient's heart based on at least one of a plurality of patient characteristics. The model heart can include a plurality of segments. The exemplary systems and methods may be further configured to determine a value of electrical activity for each of a plurality of anatomic regions of the model heart based on the mapped electrical activity. Each of the plurality of anatomic regions can include a subset of the plurality of segments.

15 Claims, 20 Drawing Sheets

(51) Int. Cl.
*A61B 5/0408* (2006.01)
*A61B 5/044* (2006.01)
*A61B 5/0468* (2006.01)
*G16H 50/50* (2018.01)
*A61B 5/107* (2006.01)
*A61B 5/02* (2006.01)
*A61B 5/0472* (2006.01)
*A61B 5/029* (2006.01)
*A61B 5/11* (2006.01)

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |

(56) References Cited

U.S. PATENT DOCUMENTS

| | | |
|---|---|---|
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2007/0270703 A1 * | 11/2007 | He ................... A61B 5/0422 600/509 |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0029866 A1 * | 1/2013 | Sun ................... G01N 33/5061 506/9 |
| 2013/0030491 A1 | 1/2013 | Stadler et al. |

(56) References Cited

U.S. PATENT DOCUMENTS

| | | |
|---|---|---|
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0245473 A1* | 9/2013 | Ramanathan ........ A61B 5/0402 600/509 |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045732 A1* | 2/2016 | Grenz .................... A61N 1/368 607/27 |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2017/0011197 A1* | 1/2017 | van Dam ................ G06F 19/00 |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application no. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.

(56) References Cited

OTHER PUBLICATIONS

Biffi et al., "Occurrence of Phrenic Nerve Stimulation in Cardiac Resynchronization Therapy Patients: the Role of Left Ventricular Lead Type and Placement Site," Europace, 2013; 15:77-82.

Botker MD, PhD., et al., "Electromechanical Mapping for Detection of Myocardial Viability in Patients with ischemia Cardiomyopathy," Circulation, Mar. 2001; vol. 103, No. 12, pp.

"CardioGuide System Enables Real-Time Navigation of Left Ventricular Leads During Medtronic CRT Implants," Press Release, Apr. 9, 2013, Medtronic, Inc., 2 pgs.

Cuculich, P.S., et al., "The Electrophysiological Cardiac Ventricular Substrate in Patients After Myocardial Infection" J. Am. Coll. Cardiol. 2011; 58:1893-1902.

Czerwinska et al., "Method of Segmentation of Thorax Organs Images Applied to Modeling the Cardiac Electrical Field," Engineering in Medicine and Biology Society, Proceedings of the $22^{nd}$ Annual International Conference of the IEEE, vol. 1, 23, Jul. 23, 2000.; pp. 402-405.

Dawoud, F. et al., "Inverse Electrocardiographic Imaging to Assess Electrical Dyssynchrony in Cardiac Resynchronization Therapy Patients," Computing in Cardiology, 2012; 39:993-996.

Freund et al., "A Decision-Theoretic Generalization of Online Learning and an Application to Boosting," Journal of Computer and System Sciences, 1997; 55(1):119-139.

Friedman, "Greedy Function Approximation: A Gradient Boosting Machine," Annals of Statistics, 2001; 29(5):1189-1232.

Friedman, "Stochastic Gradient Boosting," Computational Statistics and Data Analysis, 2002; 38(4):367-378.

Friedman et al., "Additive Logistic Regression: a Statistical View of Boosting," Annals of Statistics, 2000; 28(2):337-374.

Fung et al., Chapter 20, Optimization of Cardiac Resynchronization Therapy, Cardiac Resynchronization Therapy, Second Edition, Copyright 2008, Blackwell Publishing Ltd., pp. 356-373.

Ghosh et al. "Accuracy of Quadratic Versus Linear Interpolation in Noninvasive Electrocardiographic Imaging (ECGI)," Annuals of Biomedical Engineering, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" Circulation, 2008; 118:907-915. Published online Aug. 12, 2008.

Ghosh et al. "Application of L1-Norm Regularization to Epicardial Potential Solution of the Inverse Electrocardiography Problem," Annuals of Biomedical Engineering, vol. 37, No. 5, May 2009; pp. 902-912.

Ghosh et al., "Electrophysiological Substrate and Intraventricular LV Dyssynchrony in Non-ischemic Heart Failure Patients Undergoing Cardiac Resynchronization Therapy," Heart rhythm : the official journal of the Heart Rhythm Society, 2011; 8(5):692-699.

Gold et al., "Comparison of Stimulation Sites within Left Ventricular Veins on the Acute Hemodynamic Effects of Cardiac Resynchronization Therapy" Heart Rhythm, Apr. 2005; 2(4):376-381.

Gulrajani, "The Forward and Inverse Problems of Electrocardiography," IEEE Engineering in Medicine and Biology, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," Heart Rhythm, Sep. 2011; 8(9): 1469-1475.

"Heart Failure Management" datasheet [online]. Medtronic, Minneapolis, Minnesota, [Last updated on Jun. 3, 2013].Retrieved from the Internet: www.medtronic.com; 9 pages.

Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.

Jia et al., "Electrocardiographic Imaging of Cardiac Resynchronization Therapy in Heart Failure: Observation of Variable Electrophysiologic Responses," Heart Rhythm, vol. 3, No. 3; Mar. 1, 2006, pp. 296-310.

Kornreich, "Body Surface Potential Mapping of ST Segment Changes in Acute Myocardial Infarction," Circulation, 1993; 87: 773-782.

Lumason™, Brochure, Bracco Diagnostocs. Oct. 2014.

Medtronic Vitatron CARELINK ENCORE® Programmer Model 29901 Reference Manual, 2013, Medtronic, Inc., Minneapolis, MN.

Miri et al., "Applicability of body surface potential map in computerized optimization of biventricular pacing," Annals of Biomedical Engineering, vol. 38, No. 3, Mar. 2010, pp. 865-875.

Miri et al., "Comparison of the electrophysiologically based optimization methods with different pacing parameters in patient undergoing resynchronization treatment," 30th Annual International IEEE EMBS Conference, Aug. 2008, pp. 1741-1744.

Miri et al., "Computerized Optimization of Biventricular Pacing Using Body Surface Potential Map," 31st Annual International Conference of the IEEE EMBS, Sep. 2009, pp. 2815-2818.

Miri et al., "Efficiency of Timing Delays and Electrode Positions in Optimization of Biventricular Pacing: A Simulation Study," IEEE Transactions on Biomedical Engineering, Nov. 2009, pp. 2573-2582.

Modre et al., "Noninvasive Myocardial Activation Time Imaging: A Novel Inverse Algorithm Applied to Clinical ECG Mapping Data" IEEE Transactions on Biomedical Engineering, vol. 49; No. 10, Oct. 2002; pp. 1153-1161.

Nash et al., "An Experimental-Computational Framework for Validating in-vivo ECG Inverse Algorithms," International Journal of Bioelectromagnetism, vol. 2, No. 2, Dec. 31, 2000, 9 pp.

Potse et al., "Mathematical Modeling and Simulation of Ventricular Activation Sequences: Implications for Cardiac Resynchronization Therapy," J. of Cardiovasc. Trans. Res., 2012; 5:146-158.

Prinzen et al., "Cardiac Resynchronization Therapy State-of-the-Art of Current Applications, Guidelines, Ongoing Trials, and Areas of Controversy" Circulation, 2013; 128: 2407-2418.

Ridgeway, "The State of Boosting," Computing Science and Statistics, 1999; 31:172-181.

Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010; 21(2):219-22.

Saba et al., "Echocardiography-Guided Left Ventricular Lead Placement for Cardiac Resynchronization Therapy Results of the Speckle Tracking Assisted Resynchronization Therapy for Electrode Region Trial," Cirt. Heart Fail., May 2013; 427-434.

Silva et al., "Cardiac Resynchronization Therapy in Pediatric Congenital Heart Disease: Insights from Noninvasive Electrocardiographic Imaging" Heart Rhythm, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," Circulation, 2011; 123:1159-1166.

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012; 35(2):189-96.

Steinhaus BM., "Estimating cardiac transmembrane activation and recovery times from unipolar and bipolar extracellular electrograms: a simulation study," Circulation Research, 1989, 64:449-462.

Strik et al., "Electrical and Mechanical Ventricular Activation During Left Bundle Branch Block and Resynchronization," J. of Cardiovasc. Trans. Res., 2012; 5:117-126.

Svendsen et al., "Computational Models of Cardiac Electrical Activation," Chapter 5, Computational Nov. 2010, pp. 73-88.

Sweeney et al., "Analysis of Ventricular Activation Using Surface Electrocardiography to Predict Left Ventricular Reverse Volumetric Remodeling During Cardiac Resynchronization Therapy," Circulation, Feb. 9, 2010;121(5):626-34. Available online Jan. 25, 2010.

Sweeney et al., QRS Fusion Complex Analysis Using Wave Interference to Predict Reverse Remodeling During Cardiac Resynchronization Therapy, heart Rhythm, 2014, 11:806-813.

(56) References Cited

OTHER PUBLICATIONS

Turner et al, "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

MAPPING ELECTRICAL ACTIVITY ON A MODEL HEART

The disclosure herein relates to systems and methods for use in the mapping electrical activity on a model heart.

SUMMARY

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). In one or more embodiments, the systems, methods, and interfaces may be described as being noninvasive. For example, in some embodiments, the systems, methods, and interfaces may not need, or include, implantable devices such as leads, probes, sensors, catheters, implantable electrodes, etc. to monitor, or acquire, a plurality of cardiac signals from tissue of the patient for use in evaluating the patient and/or cardiac therapy. Instead, the systems, methods, and interfaces may use electrical measurements taken noninvasively using, e.g., a plurality of external electrodes attached to the skin of a patient about the patient's torso.

One exemplary system may include an electrode apparatus. The electrode apparatus can include a plurality of external electrodes to monitor electrical activity from tissue of a patient. The exemplary system can include computing apparatus that include processing circuitry and that is coupled to the electrode apparatus. The computing apparatus can be configured to monitor electrical activity from the patient using the plurality of external electrodes. The computing apparatus can be further configured to provide a model heart representative of the patient's heart based on at least one of a plurality of patient characteristics. The model heart can include a plurality of segments. The computing apparatus can be further configured to map the monitored electrical activity onto the plurality of segments of the model heart. The computing apparatus can be further configured to determine a value of electrical activity for each of a plurality of anatomic regions of the model heart based on the mapped electrical activity. Each of the plurality of anatomic regions comprises a subset of the plurality of segments.

In at least one embodiment, an exemplary method can include monitoring electrical activity from the patient using a plurality of external electrodes on a torso of a patient. The exemplary method can further include providing a model heart representative of the patient's heart based on at least one of a plurality of patient characteristics. The model heart comprises a plurality of segments. The exemplary method can further include mapping the monitored electrical activity onto the plurality of segments of the model heart. The exemplary method can further include determining a value of electrical activity for each of a plurality of anatomic regions of the model heart based on the mapped electrical activity. Each of the plurality of anatomic regions comprises a subset of the plurality of segments.

In at least one embodiment, an exemplary system can include an electrode apparatus. The electrode apparatus can include a plurality of external electrodes to monitor electrical activity from tissue of a patient. The exemplary system can include computing apparatus that include processing circuitry and that is coupled to the electrode apparatus. The computing apparatus can be configured to monitor electrical activity from the patient using the plurality of external electrodes. The computing apparatus can be further configured to provide a model heart representative of the patient's heart based on at least one of a plurality of patient characteristics. The model heart comprises a plurality of anatomic regions. The computing apparatus can be further configured to map the monitored electrical activity onto the plurality of anatomic regions of the model heart. The computing apparatus can be further configured to determine an indication of scar risk based on the monitored electrical activity mapped on the plurality of anatomic regions. The exemplary system can further include a display. The display can include a graphical user interface configured to assist a user in evaluating patient cardiac health. The computing apparatus can be further configured to display on the display the model heart. The computing apparatus can be further configured to display on the display the mapped electrical activity. The computing apparatus can be further configured to display on the display an identification on the model heart of the determined indication of scar risk.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
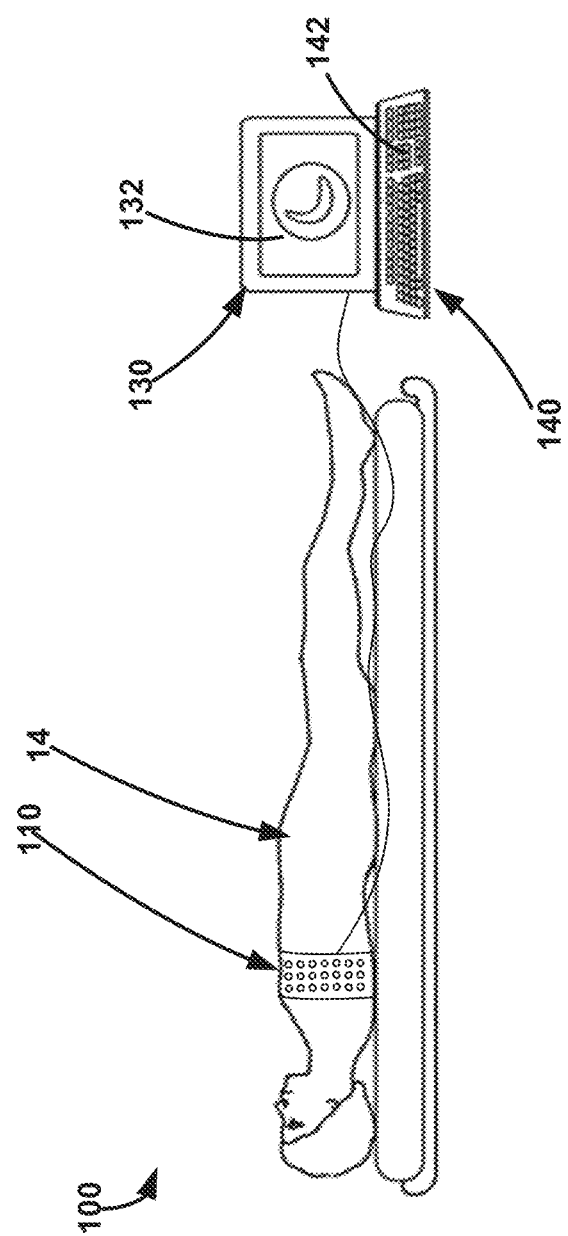
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-16. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Various exemplary systems, methods, and interfaces described herein may be configured to use electrode apparatus including external electrodes, display apparatus, and computing apparatus to noninvasively assist a user (e.g., a physician) in the evaluation of a patient's cardiac condition. Cardiac electrical activity can be monitored and/or detected using unipolar electrocardiogram (ECG) recordings using the external electrodes. The electrical activity can be mapped to a model heart by selecting a particular model heart from a plurality of model hearts based on at least one characteristic of the patient. The characteristic of the patient can include at least one of age, gender, height, chest circumference, heart chamber dimensions, ventricular ejection fraction, type of cardiomyopathy, and duration of QRS complex on 12-lead ECG, among other characteristics. The model heart can be divided into anatomic regions and the electrical activity over each of the anatomic regions can be analyzed. For example, the electrical activity over an anatomic region can be averaged for that anatomic region. Adjacent and/or other anatomic regions can be compared and/or analyzed in order to determine a condition of the patient's heart. As an example, two adjacent anatomic regions with particular electrical activity can be determined to experience slow conduction or conduction block conditions. Such electrical activity may be measured and displayed, or conveyed, to someone aiding the patient by a system which acquires the ECG signals and generates various metrics of electrical activation times (e.g., depolarization) and/or peak-to-peak voltage values measured from various ECG locations. Electrical activation times can be representative of depolarization of cardiac tissue that propagates through the torso of the patient.

An exemplary system 100 including electrode apparatus 110, display apparatus 130, and computing apparatus 140 is depicted in FIG. 1. The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) for pre-procedural and intra-procedural planning for implantation of a left ventricular (LV) lead or a leadless LV pacer, among other types of implantations. An exemplary leadless LV pacer comprises the MICRI™ commercially available from Medtronic, Inc. located in Minneapolis, Minn.

For example, the exemplary systems, methods, and interfaces may provide image guided navigation that may be used to navigate leads including electrodes, leadless electrodes, wireless electrodes, catheters, etc., within the patient's body while also providing noninvasive cardiac therapy evaluation including pre-procedural and/or intra-procedural planning for cardiac implantation of a lead or leadless pacer. Exemplary systems and methods that use imaging apparatus and/or electrode apparatus may be described in U.S. Patent Publication No. 2014/0371832 filed on Jun. 12, 2013 and entitled "Implantable Electrode Location Selection," U.S. Patent Publication No. 2014/0371833 filed on Jun. 12, 2013 and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical Electrical Vectors," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate cardiac implantation apparatus within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac activation times, peak-to-peak data, cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating during pre-procedural and/or intra-procedural planning for cardiac implantation of a lead or leadless pacer.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac implantation and/or therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, two-dimensional and three-dimensional model hearts for a plurality of different model humans, two-dimensional and three-dimensional model torsos for a plurality of different model humans, cardiac conduction indicators, scar risk indicators, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, image construction algorithms, inverse problem processes for image and/or data projection, two-dimensional and three-dimensional image and/or data projection processes, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, one or metrics generated, or derived, from electrical signal/waveform data from the electrode apparatus 110 (e.g., peak-to-peak values, activation times, metrics of cardiac electrical heterogeneity and desynchrony, etc.), dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
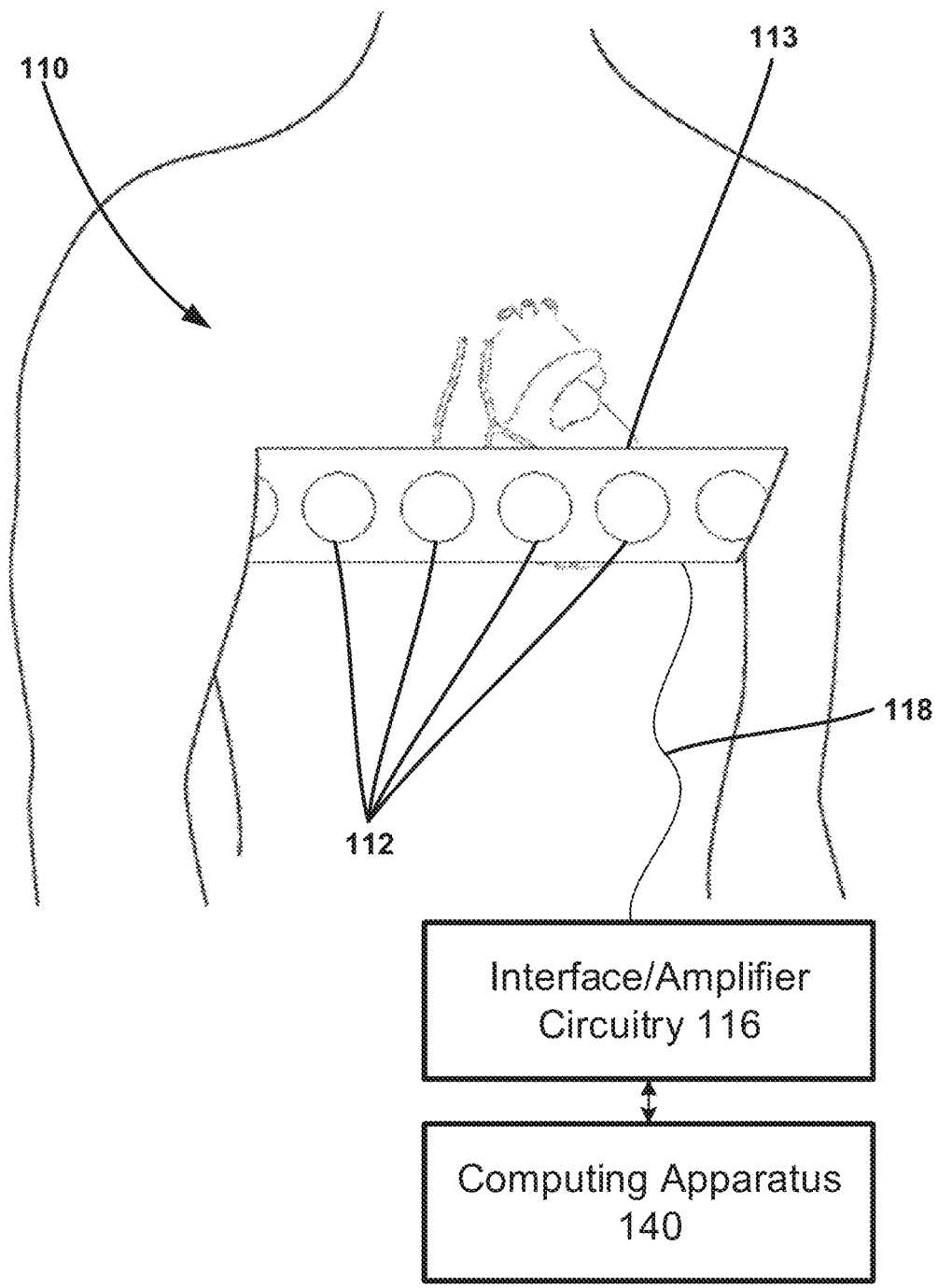
FIG. 2 is a diagram of an exemplary external electrode apparatus for measuring torso-surface potentials.
Figure 3:
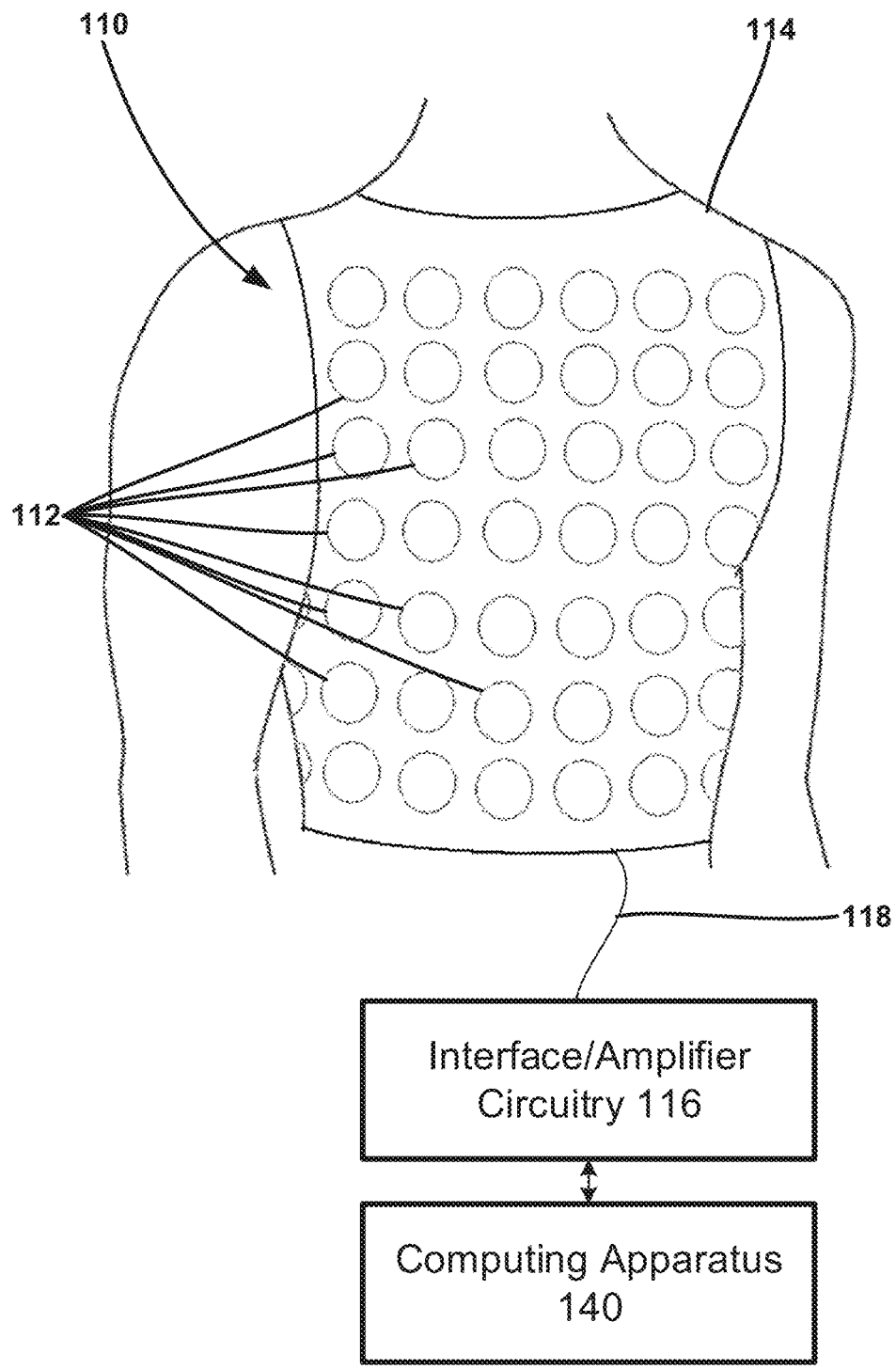
FIG. 3 is a diagram of an exemplary external electrode apparatus for measuring torso-surface potentials.

Data generated using electrode apparatus 110 as shown in FIG. 1 and in FIG. 2-3 may be useful to evaluate a pre-procedural and/or intra-procedural plan for cardiac implantation and/or therapy. For example, surrogate electrical activation information or data of one or more regions of a patient's heart may be monitored, or determined, using the electrode apparatus 110. More specifically, the exemplary electrode apparatus 110 may be configured to measure body-surface potentials, or torso-surface potentials, of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the electrical activity (e.g., torso-surface potential signals)

sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. The computing apparatus 140 may be configured to analyze the signals from the electrodes 112 to provide peak-to-peak values, e.g., representative of actual, or local, peak-to-peak values of one or more regions of the patient's heart as will be further described herein. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a pre-procedural and/or intra-procedural implantation plan for the patient.

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the anterior, lateral, posterolateral, anterolateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In one or more embodiments, the vest 114 may include 17 or more anterior electrodes positionable proximate the anterior torso of the patient, and 39 or more posterior electrodes positionable proximate the anterior torso of the patient. In some examples, there may be about 25 electrodes 112 to about 256 electrodes 112 distributed around the torso of the patient 14, though other configurations may have more or less electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. That is, the approximation of activation times of the patient's heart can be based on a mapping of activation times from monitored electrical activity being correlated to a model heart and solving an inverse problem to determine an approximate activation time for a region and/or location of the patient's heart, as is described in association with FIGS. 8-11B. Further, for example, peak-to-peak values of different regions of a patient's heart can be approximated from surface electrocardiogram (ECG) signals measured using surface electrodes in proximity to surface areas corresponding to the different regions of the patient's heart.

The exemplary systems, methods, and interfaces may be used to provide noninvasive assistance to a user in the pre-procedural and/or intra-procedural planning of cardiac implantation for therapy related to a patient's cardiac health or status, and/or the evaluation of cardiac therapy post-implantation by use of the electrode apparatus 110 (e.g., cardiac therapy being presently-delivered to a patient during implantation or after implantation). Further, the exemplary systems, methods, and interfaces may be used to assist a user in the planning of cardiac implantation within and/or therapy being delivered to a patient.

Electrical activity monitored by the plurality of external electrodes can be used to solve an inverse problem of electrocardiography. The solution of the inverse problem can be based on a projection of locations at which the torso-surface potentials are measured, monitored by the external electrodes, onto a model torso. The torso-surface potentials can be projected onto locations on the model heart based on a geometric relationship between the model heart and the model torso. As the model heart is selected based on at least one characteristic of a patient, the model torso associated with the model heart can correspond to the physical torso of the patient based on the at least one characteristic of the patient. As an example, a chest circumference of the patient can be used to select the model heart, and thus, the model torso associated with the model heart would correspond to the patient's physical torso based on the chest circumference used. In this way, solving the inverse problem can include estimating potentials and/or activation times in a patient's heart based on a relationship between the heart locations of the torso-surface potentials and torso model, and the torso model to model heart, all used to map corresponding torso-surface potentials to the model heart. The torso model can include typical geometric locations of each of its corresponding plurality of external electrodes. The geometric locations of the plurality of external electrodes of the torso model can be correlated with corresponding geometric locations of a model heart.

From these torso-surface potential signals, a metric of electrical activity can be calculated and also mapped to the corresponding locations of the model heart. A metric of electrical activity can include any one of activation times, gradient of activation time, peak-to-peak QRS voltages, etc. Low amplitude peak-to-peak QRS voltages can be indicative of scarring of heart tissue. The metrics of electrical activity can include metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces. The metrics of electrical heterogeneity information can include a metric of mean right ventricular activation time (RVAT) of electrodes on the right side of the torso of the patient. A metric of RVAT may be determined from electrodes on both the anterior and posterior surfaces. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso.

Figure 4:
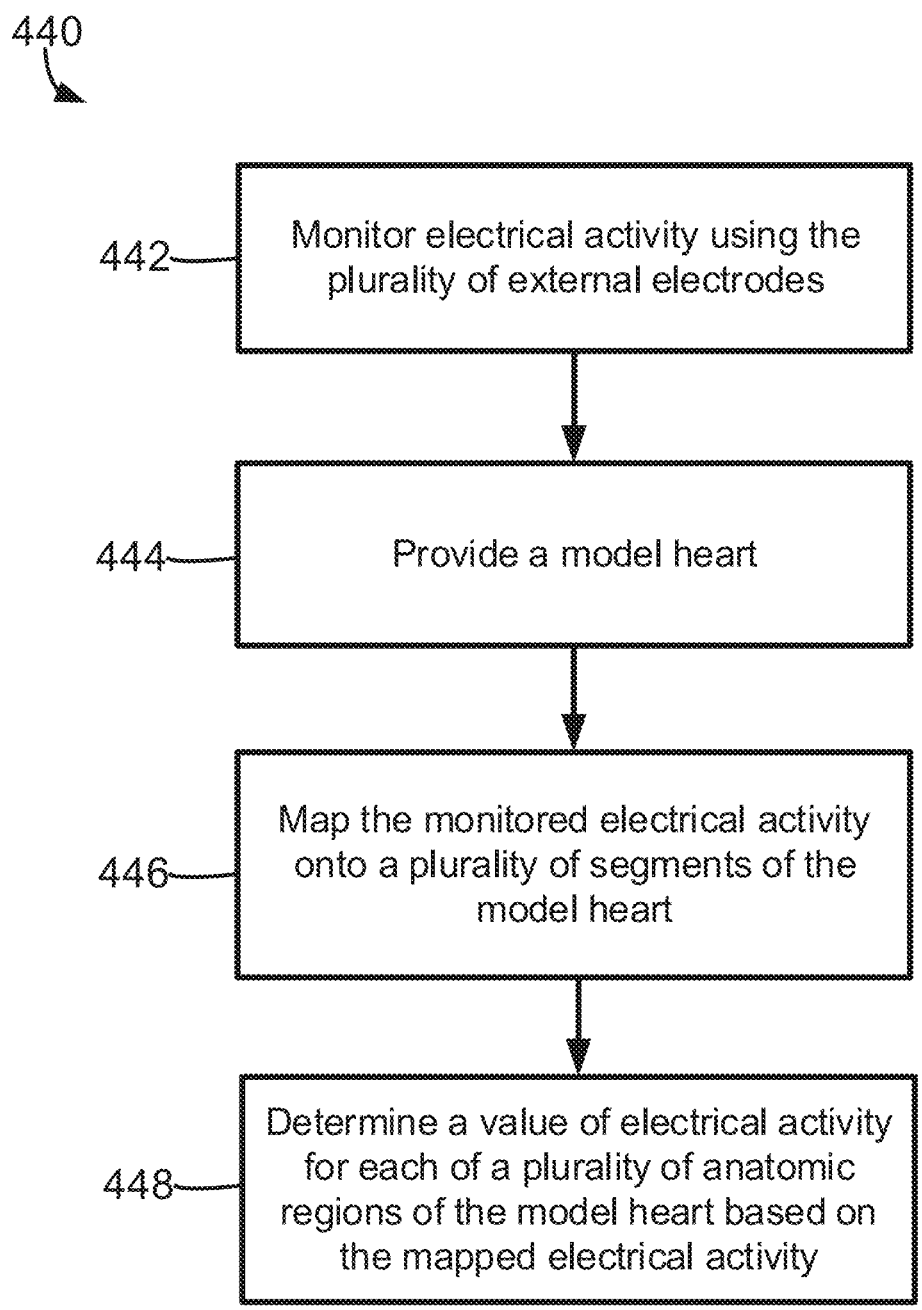
FIG. 4 is a block diagram of an exemplary method for use in mapping electrical activity on a model heart.

The block diagram of FIG. 4 is an exemplary method 440 of mapping, or regionalizing, electrical activity on a model heart. The method 440 can include monitoring electrical activity using a plurality of external electrodes 442 such as the electrodes 112 of the electrode apparatus 110 described herein with reference to FIGS. 1-3. The monitored electrical activity can include torso-surface potential signals monitored at a plurality of locations associated with each of the plurality of external electrodes. The monitored electrical activity can be used to determine, or generate, cardiac activation times and/or peak-to-peak QRS voltages. As used herein, peak-to-peak voltage can refer to a difference between a maximum and minimum voltage of each location on a model during the QRS wave that coincides with and is generated by the depolarization of the heart. As an example, for a typical unipolar electrogram the maximum voltage can occur at a top of an upward deflection of an R-wave within a QRS complex, a minimum voltage can occur at the bottom of a downward deflection of an S-wave of a QRS complex, and the difference in amplitudes between the maximum and minimum represents the peak-to-peak voltage.

The method 440 can further include providing a model heart 444. The model heart may be a two-dimensional or three-dimensional representation of the patient's heart and may include a plurality of segments. In one or more embodiments, the plurality of segments may be defined as surface portions of the model heart. Further, in one or more embodiments, each segment may be separate from each other. Further, it may be described that each of the plurality of segments may be a polygon such as, for example, a triangle. The model heart may be described as being defined by, or made up of, a plurality of vertices for representation or approximating the exterior surface of the heart. Three of the vertices may be connected via lines, or edges, to define a planar triangular surface (e.g., a polygon). A plurality of planar triangular surfaces may be used to form the complex shape of the heart. In other words, the model heart may be described as being a model heart using polygonal modeling using a plurality of vertices linked to provide a plurality of edges (e.g., lines between verifies) and plurality of polygons (e.g., triangles, quads, etc.), which may form a plurality of non-self-intersecting meshes. In one embodiment, each segment may correspond to one of the plurality of polygons. For example, each triangle formed by three vertices (or polygon formed by more than three vertices) may be, or define, a segment. In another embodiment, each segment may correspond to more than one of the plurality of polygons. For example, two or more triangles, each formed by three vertices, (or polygons, each formed by more than three vertices) may be, or define, a segment. In this way, the resolution of the anatomic regions may be the same as or less than the polygonal modelling of the model heart. In at least one example, the segments can be defined by existing clinical standards (e.g., according to an American Heart Association (AHA) model).

The method 440 can further include mapping the monitored electrical activity onto the plurality of segments of the model heart 446. More details regarding at least one embodiment for mapping, or projecting, the monitored electrical activity onto the plurality of segments of the model heart 446 are described further herein with respect to FIG. 6. In one example, the model heart can be provided with segments already defined, or divided, and the monitored electrical activity can be projected on the segments based on the locations (of the torso surface of the patient) of the electrodes from which the electrical activity was monitored. In another example, the model heart can be provided without the segments defined or "divided out." When the model heart is provided without defined segments, the model heart can be segmented before or after mapping electrical activity onto the model heart. That is, the model heart can be provided, divided into segments and then the electrical activity can be mapped onto those segments.

The method 440 can further include determining a value of electrical activity for each of a plurality of anatomic regions of the model heart based on the mapped electrical activity 448. The plurality of anatomic regions of the model heart can each include a plurality of segments. That is, a first anatomic region can include a first plurality of segments of the model heart and a second anatomic region can include a second plurality of segments of the model heart. In determining the value of electrical activity for an anatomic region, the value can incorporate values from electrical activity from each of the segments within that anatomic region. As an example, each of the first plurality of segments of the model heart in the first anatomic region can have electrical activity that includes activation times. The activations times of the first plurality of segments can be averaged, or combined in some fashion (e.g., median, maximum, average, etc.), and the first anatomic region can be associated with the averaged activation times for that region.

Figure 5:
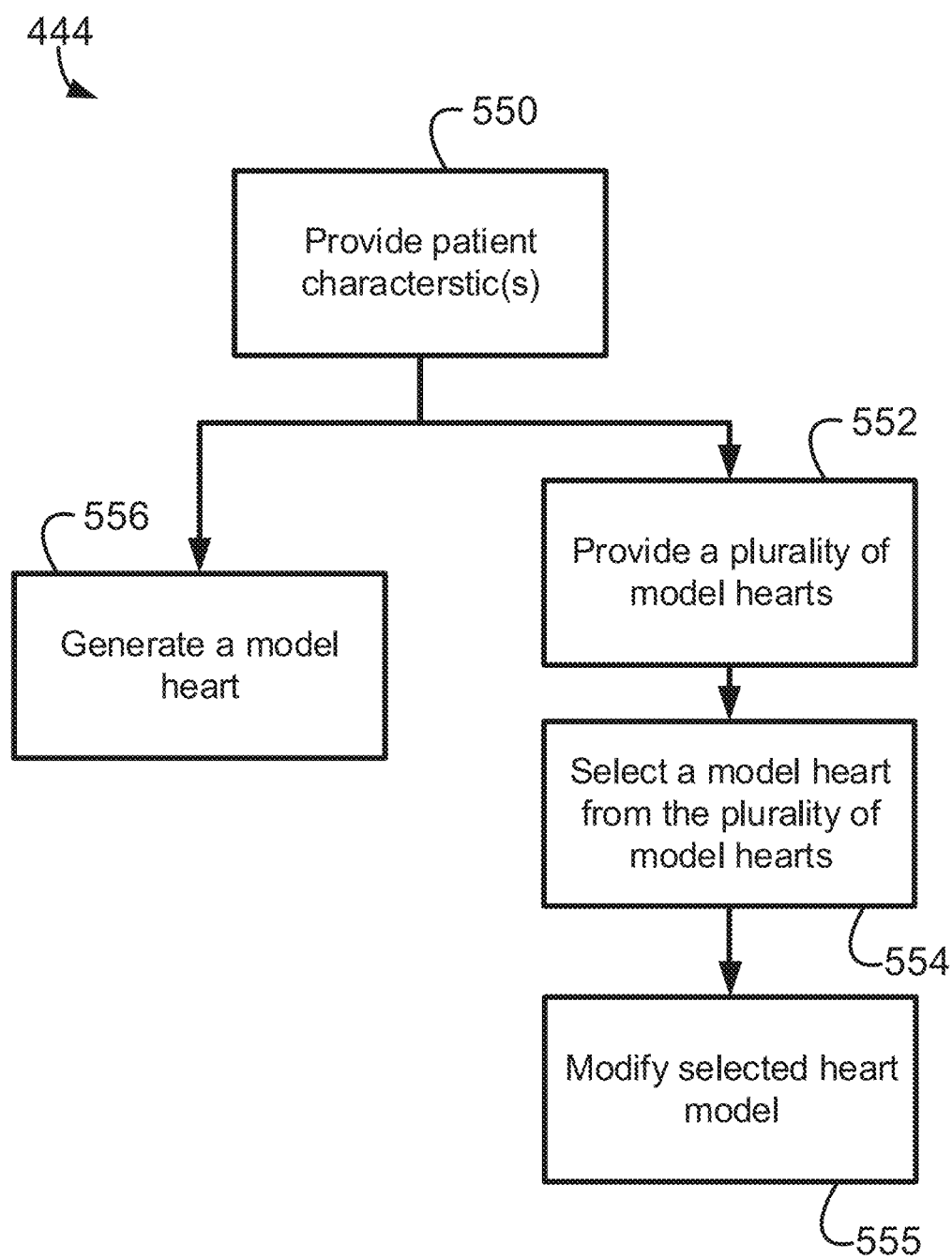
FIG. 5 is a block diagram of an exemplary method of providing a model heart for use, for example, in the method of FIG. 4.

A detailed block diagram of providing a model heart 444 is depicted in FIG. 5. The method 444 of FIG. 5 can be described as one exemplary embodiment of method step 444 in method 440 described in association with FIG. 4. That is, providing a model heart 444 of method 440 can include the steps of method 444 in FIG. 5. Generally, it may be described that providing a model heart 444 may include one or both of selecting a model heart from a plurality of model hearts based on one or more patient characteristics and generating a model heart based on one or more patient characteristics.

The method 444 may include providing one or more patient characteristics 550. The one or more patient characteristics may be used to select, generate, and modify the model heart for the patient. In other words, the model heart may be "picked" or "created" based on the one or more characteristics of the patient such that the model heart ultimately provided by method 444 approximates the patient's heart without requiring time-consuming and potentially expensive imaging procedures to obtain a model of the patient's heart. The characteristic of the patient can include at least one of age, gender, height, weight, chest circumference, heart chamber dimensions (e.g., end-systolic and end-diastolic diameters of at least one of the left and right ventricles), ventricular ejection fraction, type of cardiomyopathy, duration of QRS complex on 12-lead ECG, among other characteristics. Further, it is understood that the exemplary methods and processes descried herein may be configured to use one or a plurality of the patient characteristics to select, generate, and/or modify a model heart for the patient.

The patient characteristics can then be used to provide a model heart. For example, the method 444 may further include providing a plurality of model hearts 552. As described above, the plurality of model hearts can be provided from a library and/or catalogue of model hearts that have already been generated, for example, based on one or more various patients (different from that who is presently being evaluated) and/or based on one or more known cardiac models approximating the size, shape, and structure of a human heart. Each model heart of the plurality of model hearts may be correlated to, or correspond with, patient characteristics from which the model hearts where derived or generated from. For example, if each model heart were acquired from imaging of a patient (different from that who is presently being evaluated), each model heart may be associated with the plurality of patient characteristics of the such patient. Further, if each model heart were acquired from imaging of a plurality of patients, each model heart may be associated with the plurality of patient characteristics that may be compiled from the plurality of patients. In other words, each of the model hearts may come with, or be associated with, a plurality of patient characteristics that were generated, or derived, from the patients whose hearts were modelled for the model hearts.

Further, the plurality of model hearts of the library can be described as being already generated, or pre-generated, such that, for example, patients do not need to be imaged or are being scanned using computed tomography (CT), magnetic resonance imaging (MRI), etc. In this way, the exemplary systems and methods described herein may be less cumbersome and more cost effective.

The method 444 may further include selecting a model heart from the plurality of model hearts 554 based on the provided one or more patient characteristics without the use of imaging or scanning (MRI, CT, etc.) of the patient's heart. In other words, the provided patient characteristics of the present patient may be attempted to be approximately "matched" with the patient characteristics of a corresponding model heart. In this way, the selected model heart, although not generated from imaging of the present patient, may be described as being representative of the present patient's heart. For example, the model heart may be selected based on age, gender, and chest circumference, and thus, the model heart of the library and/or catalogue of model hearts that best corresponds to, or correlates with, the patient's age, gender, and chest circumference may be selected. Further, for example, the model heart may be selected based on height, age, and ventricular ejection, and thus, the model heart of the library and/or catalogue of model hearts that best corresponds to, or correlates with, the patient's height, age, weight, chest circumference and heart dimensions (e.g., left ventricular end-systolic and end-diastolic diameters), and thus, the model heart of the library and/or catalogue of model hearts that best corresponds to, or correlates with, the patients height, age, and dimensions may be selected.

Further, the method 444 may further include, in conjunction or alternative to the processes 552, 554, generating a model heart 556 based on one or more patient characteristics without the use of imaging or scanning (MRI, CT, etc.) of the patient's heart. For example, the patient characteristics may be input in a model heart generation process (e.g., three-dimensional model heart generation process) that may then generate the model heart based on such patient characteristics. The model heart generation process may utilize known sizes, shapes, and locations of portions, regions, and structures of the human heart correlated to the patient characteristics, and then the model heart may be generated using the inputted patient characteristics. For example, the size of a patient's heart may be approximated based on a width and/or length of the patient's heart and/or torso, ejection fraction, heart dimensions (e.g., left ventricular end-systolic and/or end-diastolic diameters), coronary anatomy from venogram, and chest circumference. Thus, the model heart generation process may include calculations, or algorithms, that determine the size of the model heart based on the width and/or length of the patient's heart and/or torso, input ejection fraction, heart dimensions, and chest circumference of the patient.

Further, the method 444 may include modifying a selected model heart using the inputted, or provided, patient characteristics 555. For example, the model heart can be provided by using a model heart from the plurality of model hearts 554 as a guide and modifying the model heart to be more in line with the characteristic of the patient using the modifying process 555. As an example, a model heart of the plurality of model hearts may be from a previous patient whose characteristics may be relatively closes to the patient's characteristics but in order to get a more accurate model heart, the model heart may be modified to compensate for any differences between the characteristics of the previous patient and the patient. In other words, the selected model heart can be modified in line with the differences in characteristics of the patients. If the model heart selected is derived from a previous patient that has a characteristic that is difference that that of the present patient, such as chest circumference, then selected model heart can be modified to account for the difference (e.g., a smaller or larger chest circumference). In this way, a combination of a library of model hearts and a modification of the selected model heart for the current patient can be used.

Figure 6:
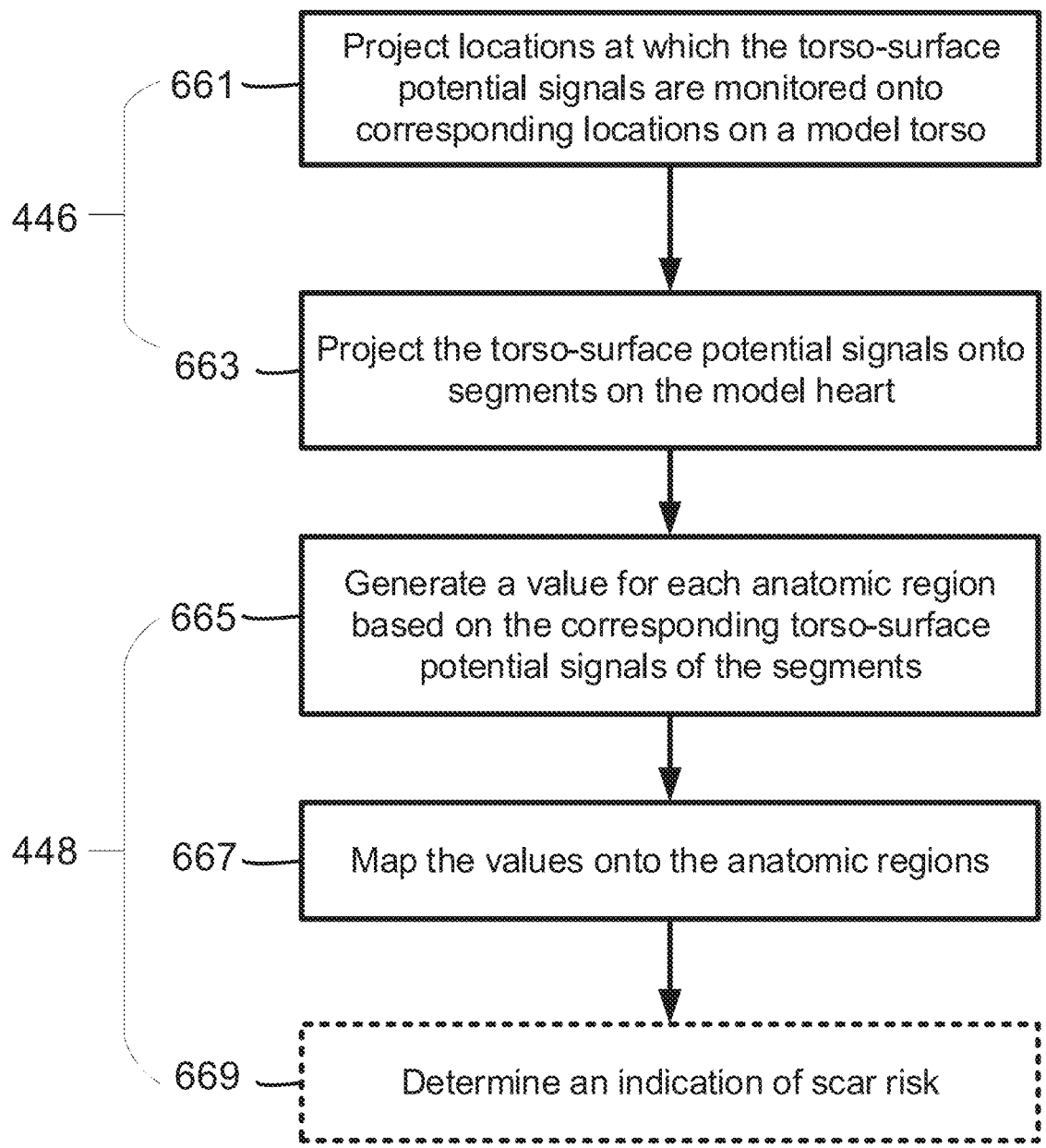
FIG. 6 is a block diagram of an exemplary method of mapping the electrical activity on the model heart for use, for example, in the method of FIG. 4.

FIG. 6 is a detailed block diagram of mapping electrical activity onto a plurality of anatomic regions of the model heart 446. The method 446 of FIG. 6 can be described as one exemplary embodiment of method step 446 in method 440 described in association with FIG. 4. That is, mapping electrical activity onto a plurality of anatomic regions of the model heart 446 of method 440 can include the steps of method 446 in FIG. 6. The method 446 can include projecting locations at which torso-surface potential signals are monitored onto corresponding locations on a model torso 661. The model torso can be associated with a provided and/or selected model heart. That is, the model torso of the previous patient who is associated with the model heart can be used to project the locations of the torso-surface potential signals onto.

The method 446 of FIG. 6 can further include projecting the torso-surface potential signals onto segments on the model heart 663. The torso-surface potential signals can be projected onto segments on the model heart based on a geometric relationship between the model heart and the model torso. As an example, the torso of the patient is correlated with locations of segments on the model torso and the model torso has a geometric relationship to the segment locations on the model heart. In this way, the locations of the torso-surface potential signals can be correlated to segment locations on the model heart.

The method 448 of FIG. 6 can further include generating a value for each anatomic region based on the corresponding torso-surface potential signals of the segments 665. Generating the value for each anatomic region can include combining values from each of a plurality of segments within each anatomic region. For example, the generated value can include at least one of an activation time and/or a peak-to-peak voltage associated with the torso-surface potential signals that were projected onto the plurality of segments within each anatomic region. In at least one example, the generated value can include averaging activation times of these plurality of segments that are within and/or within a threshold proximity to the anatomic region. In at least one example, the generated value can include averaging peak-to-peak voltages that are within and/or within a threshold proximity to the anatomic region. The method 448 of FIG. 6 can further include mapping the values onto the anatomic regions 667. The values can be mapped onto the anatomic regions by numerical display, graphical display, color-coordinated or grey shading display, etc., that is further described in association with FIGS. 8-11B.

The method 448 of FIG. 6 can further optionally include determining an indication of scar risk 669. In at least one example, a determination of scar risk can be based on peak-to-peak values that are below a particular threshold. In at least one example, an anatomic region can be determined to include a scar risk in response to the anatomic region including an averaged peak-to-peak value that is below a threshold value. The anatomic region with the scar risk can be tagged with an indicator that indicates the anatomic region has a higher risk of scar. Implanters of a lead or leadless pacer may want to target areas of late electrical activation without this scar risk indicator as a preliminary implant target region.

Figure 7:
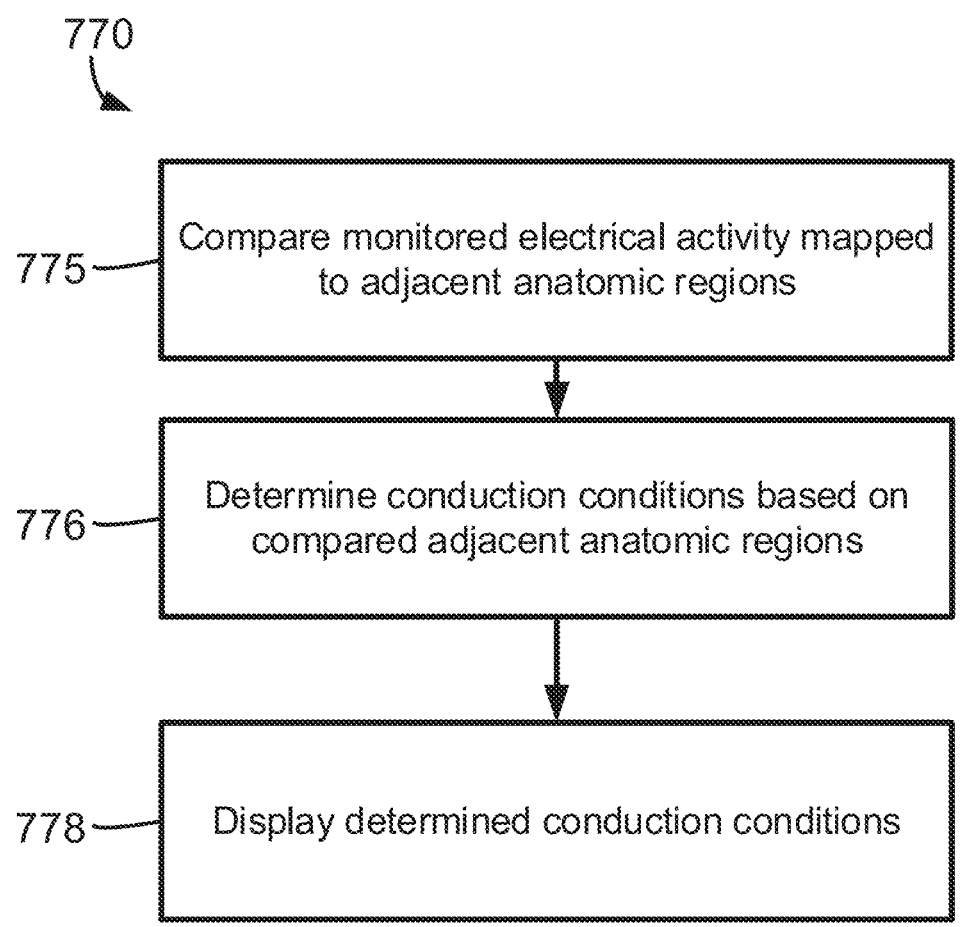
FIG. 7 is a block diagram of an exemplary method of determining a conduction condition.

The block diagram of FIG. 7 is an exemplary method 770 of determining and mapping conductive conditions such as slow conduction activity, a conduction block, etc., More specifically, the method 770 can include comparing monitored electrical activity mapped to adjacent anatomic regions 775, and then determining conduction conditions based on compared adjacent anatomic regions 776. As an example, a first anatomic region can be adjacent to a second anatomic region. The electrical activity of the first anatomic region can be compared to the electrical activity of the second anatomic region. The electrical activity compared can include activation times, peak-to-peak voltage values, etc.

In other words, conduction conditions can be determined in response to a high gradient between the electrical activity of adjacent first and second anatomic regions. Adjacent anatomic regions with a high gradient of difference in electrical activity illustrates that the conduction is having difficulty passing from one anatomic region to the next adjacent anatomic region. For example, a percentage difference may be calculated between the values (e.g., peak-to-peak values) of mapped anatomic regions, and if the percentage difference exceeds a selected threshold indication of a conduction condition (e.g., such as a block), it may be determined that a conduction condition exists between such anatomic regions.

Figure 9A:
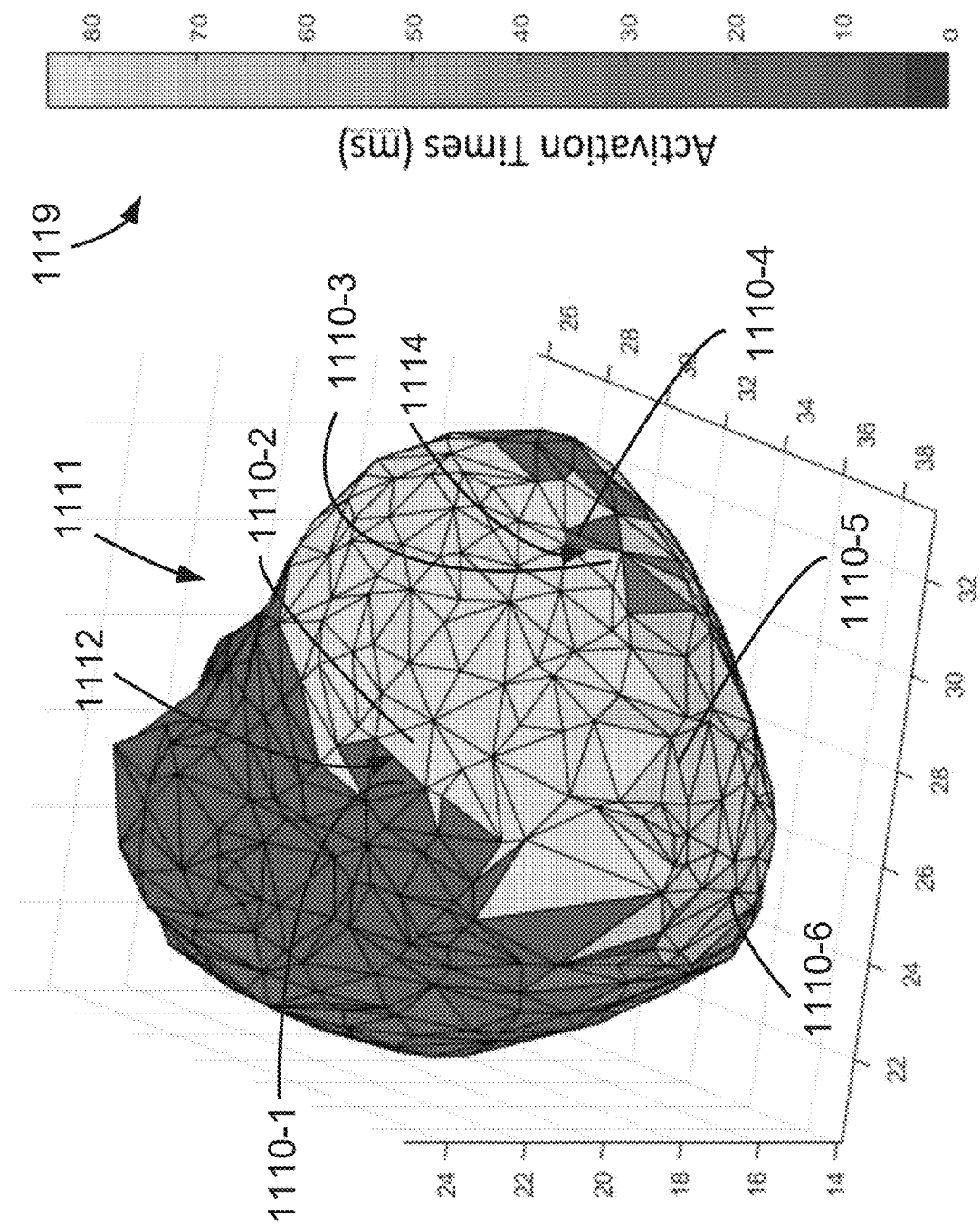
FIG. 9A depicts an exemplary model heart illustrating a few conduction conditions.
Figure 9B:
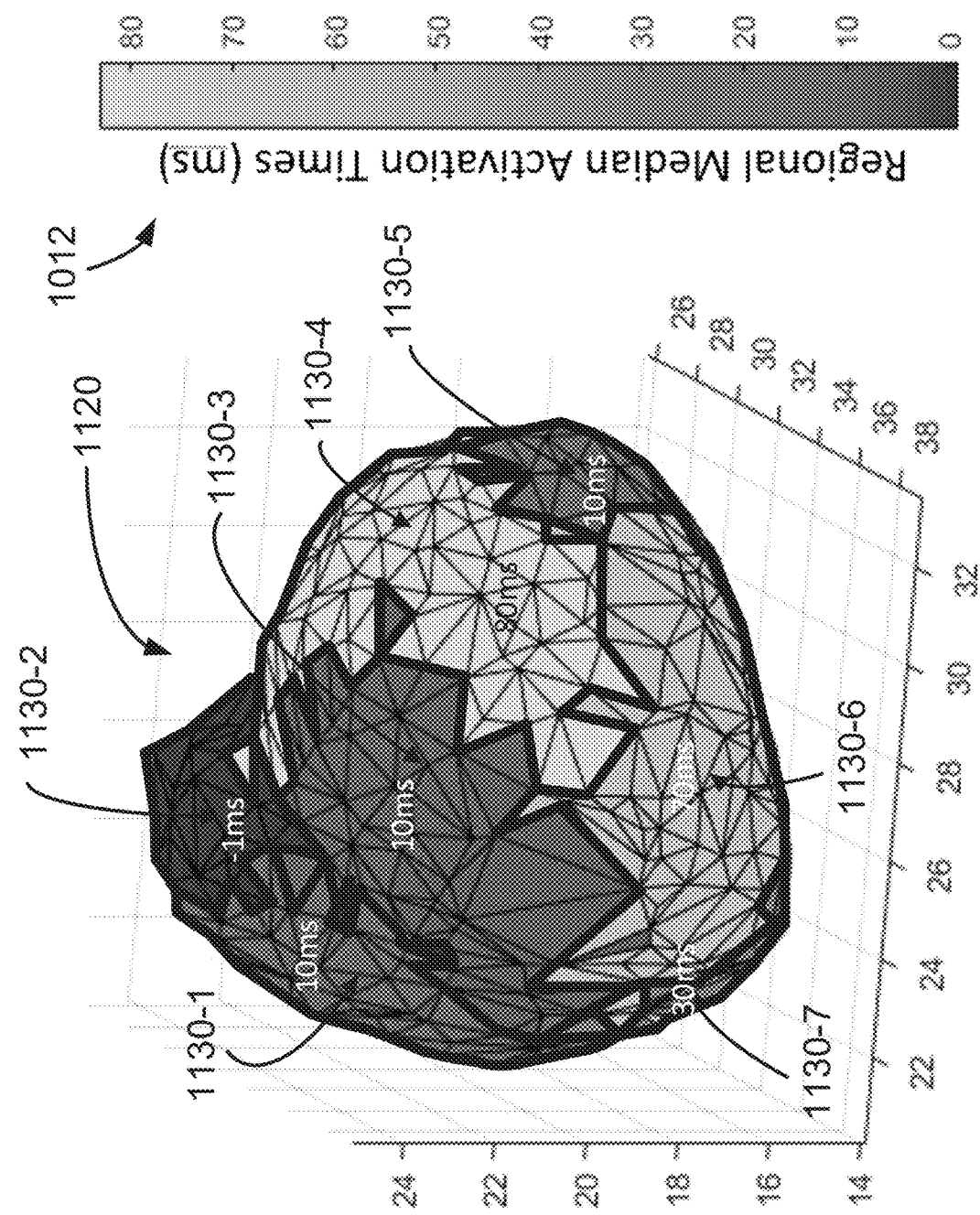
FIG. 9B depicts an exemplary model heart illustrating a plurality of anatomic regions and cardiac electrical activation times mapped thereto.

The method 770 may further include display of the conduction conditions 778 such as shown in FIG. 9B. For example, a graphical element (e.g., a line) indicative of a location of the determined slow conduction or conduction block conditions may be depicted, or displayed, on the model heart, e.g., between adjacent anatomic regions that were determined to have a conduction condition. In response to electrical heterogeneity during pacing not being reduced by more than a selected threshold at the intersection of these adjacent anatomic regions, an implanter may use information from the electrical activity during pacing to target a lead location (for example, target anatomic regions that circumvent the line of conduction block, etc.).

Figure 8:
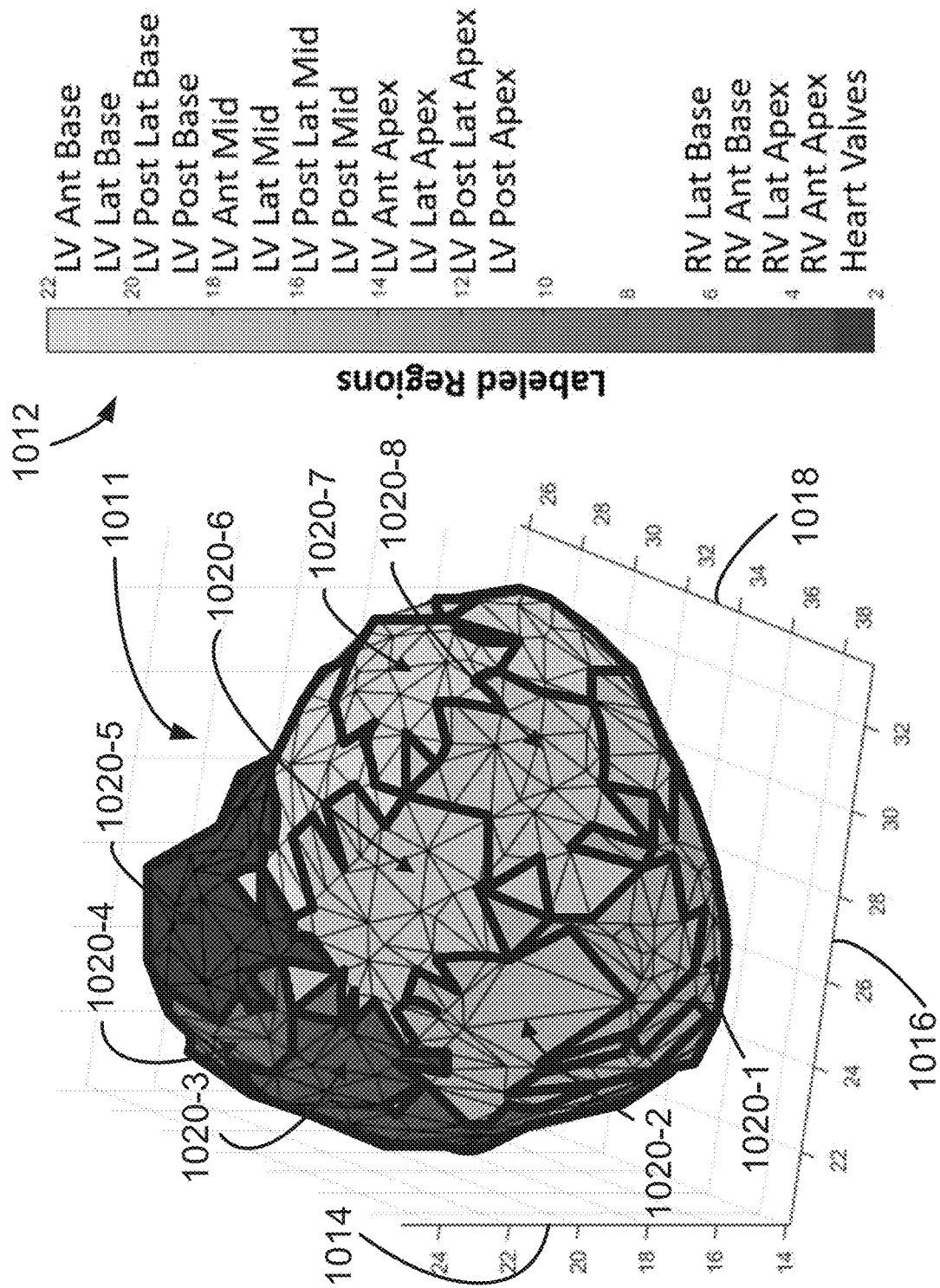
FIG. 8 depicts an exemplary model heart including a plurality of anatomic regions.

FIG. 8 depicts an exemplary model heart 1011 including a plurality of anatomic regions 1020 using the exemplary systems and methods described herein with reference to FIGS. 1-7. Thus, the exemplary model heart 1011 including a plurality of anatomic regions 1020 and electricity activity mapped thereto may have been generated, or created, without imaging the patient's heart, and instead, using one or more patient characteristics to provide the model heart 1011 and map the electrical activity thereon. As shown, a labelled regions indicator 1012 may be depicted proximate the model heart 1011 and may be used to indicate a particular anatomic region of the model heart 1011. As is illustrated in FIG. 8, anatomic region 1020-5 corresponds to the color/shade of the labelled regions indicator 1012 that indicates "heart valves." This region of the heart may not have electrically active myocardium, but may be included in this diagram in order to fully capture the geometry of the heart in order for other, electrically active portions of the myocardium to be properly illustrated and its corresponding electrical activity properly mapped and/or projected.

Further, as further described herein with reference to process 444, the model heart 1011 can be described as a three-dimensional (3D) representation that extends in the x, y, and z planes, indicated by axes 1016 (x-plane), 1014 (y-plane), and 1018 (z-plane) and as including a plurality of anatomic regions, a few of which are labeled as 1020-1, 1020-2, 1020-3, 1020-4, 1020-5, 1020-6, 1020-7, and 1020-8 (hereinafter referred to collectively as 1020). Each of the anatomic regions 1020 can include a plurality of segments (e.g., the triangular shapes illustrated) that make up that corresponding anatomic region. Put another way, each of the anatomic regions 1020 can include a subset of the plurality of segments that cover the entire heart model 1011. Each of the anatomic regions 1020 can be indicated by a corresponding shade/color of the labelled regions indicator 1012 of the model heart 1011. As an example, anatomic region 1020-7 can correspond to a shade/color on the labelled regions indicator 1012 that corresponds to the left ventricular posterior lateral base (LV Post Lat Base). That is, all of the segments in anatomic region 1020-7 are of a same shade/color from the labelled regions indicator 1012. Further, anatomic region 1020-3 can correspond to a shade/color on the labelled regions indicator 1012 that corresponds to the right ventricular anterior apex (RV Ant Apex). As will be described further in association with FIG. 9A, the anatomic regions 1020 can each experience a different level or value of electrical activity. In at least one example, due to artifacts of the mapping, at least one segment (e.g., triangular segment) of a particular region can be non-contiguous with other segments of that particular region. As illustrated in FIG. 8, bolded lines can indicate a boundary between two labeled regions. However, in at least one example, the bolded lines may be omitted and are used here only for illustrative purposes.

As illustrated in FIG. 9A, a model heart 1111 can include a plurality of segments, a few that border other segments with differing activation times and are labeled as 1110-1, 1110-2, 1110-3, 1110-4 (hereinafter referred to collectively as 1110). The segments 1110 can each experience a different level or value of electrical activity, indicated by a correspondence between the shade/color of the electrical activity indicator 1119 and those on the model heart 1111. The electrical activity can be mapped to the segments 1110 of the model heart 1111. The model heart 1111 illustrated in FIG. 9A illustrates segments that have not been combined and/or divided into anatomic regions, as will be further discussed in association with FIGS. 9B-9D.

In this embodiment, the electrical activity mapped about, or onto, the model heart 1111 within the segments 1110 are cardiac activation times. As described herein, the cardiac activation times may be described as being representative of the timing of the depolarization of the cardiac tissue. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

That is, a first segment 1110-1 is illustrated as having an electrical activity value, or activation time, corresponding to around twelve (12) on the indicator 1119. A second segment 1110-2 is illustrated as having an electrical activity value, or activation time, corresponding to around eighty (80) on the indicator 1119. A third 1110-3 and fourth 1110-4 segment each have electrical activity value, or activation time, corresponding to eighty (80) and around twelve (12), respectively, as well. A fifth segment 1110-5 has an electrical activity value, or activation time, corresponding to around seventy (70) on the electrical activity indicator 1119. A sixth segment 1110-6 has an electrical activity value, or activation time, corresponding to around fifty (50) on the electrical activity indictor 1119. In this embodiment, each of the mentioned segments can be surrounded by further segments of about the same or very different electrical activity values.

Further, FIG. 9A depicts an exemplary model heart 1111 illustrating, or having, a few possible conduction conditions. The first segment 1110-1 and the fourth segment 1110-4 have a similar electrical activity, as illustrated, and a second segment 1110-2 and a third segment 1110-3 have similar electrical activity. However, the adjacent first 1110-1 and second 1110-2 segments include electrical activities that may be described as varying or differing too much. That is, there is a gradient at the boundary 1112 of the first 1110-1 and second 1110-2 segments, which may indicate a conduction condition, such as slow conduction condition or a conduction block condition. Further, another example gradient of electrical activities is illustrated at a boundary 1114 between the third 1110-3 and the fourth 1110-4 segments, also indicating a conduction condition.

FIG. 9B depicts an exemplary model heart illustrating a plurality of anatomic regions and cardiac electrical activation times mapped thereto. The model heart 1120 can include a plurality of anatomic regions 1130, where each labeled region or group of regions 1130-1, 1130-2, 1130-3, 1130-4, 1130-5, 1130-6, 1130-7 indicates at least one region that a median activation time has been determined. That is, a labeled region, such as 1130-3 in FIG. 9B can include both regions 1020-2 and 1020-6 illustrated in FIG. 8 as those two regions 1020-2 and 1020-6 have a same median activation time (e.g., approximately 10 ms), as illustrated in FIG. 9B. As illustrated in FIG. 9B, bolded lines can indicate a boundary between at least two labeled regions. However, in at least one example, the bolded lines may be omitted and are used here only for illustrative purposes.

Each of the anatomic regions 1130 can include a subset of the plurality of segments across the entire heart model 1120, where a segment of the plurality of segments is illustrated by a triangular shape of the model heart 1120. The plurality of anatomic regions 1130 are illustrated with a mapping of the electrical activity of each segment illustrated in FIG. 9A being combined across each anatomic region in FIG. 9B. That is, as an example, the electrical activity of segments, illustrated in FIG. 9A, that correspond to an anatomic region can be averaged for that anatomic region, which is illustrated in FIG. 9B. Put another way, the electrical activity illustrated in FIG. 9A is on a segment-by-segment basis and is averaged, illustrated in FIG. 9B, within an anatomic region in order to be on a region-by-region basis. As described in association with FIG. 8, some anatomic regions may be associated with myocardium that are not electrically active (e.g., such as anatomic region 1020-5 in FIG. 8). In order to compensate for this, these electrically inactive portions of the myocardium of the heart can be assigned an electrical activity value of −1 ms to indicate that these are not regions of interest, as will be further described in association with FIGS. 9B-9D below.

A regional median activation time indicator 1012 is illustrated and depicts a color/shade scheme that corresponds with median activation times for each region. That is, anatomic region 1130-1 has a median activation time (e.g., the median activation time for all the segments within anatomic region 1130-1) corresponding to around ten (10) ms (shown in white within 1130-1) on the electrical activity indicator 1012. Anatomic region 1130-2 is assigned a median activation time of negative one (−1) ms on the regional median activation time indicator 1012 which indicates that this anatomical region is not activating myocardium, i.e., not activating valves and vessels. Anatomic region 1130-3 has a median activation time corresponding to around ten (10) ms, anatomic region 1130-4 has a median activation time corresponding to around eighty (80) ms (shown in black within 1130-4), and so forth.

Figure 9C:
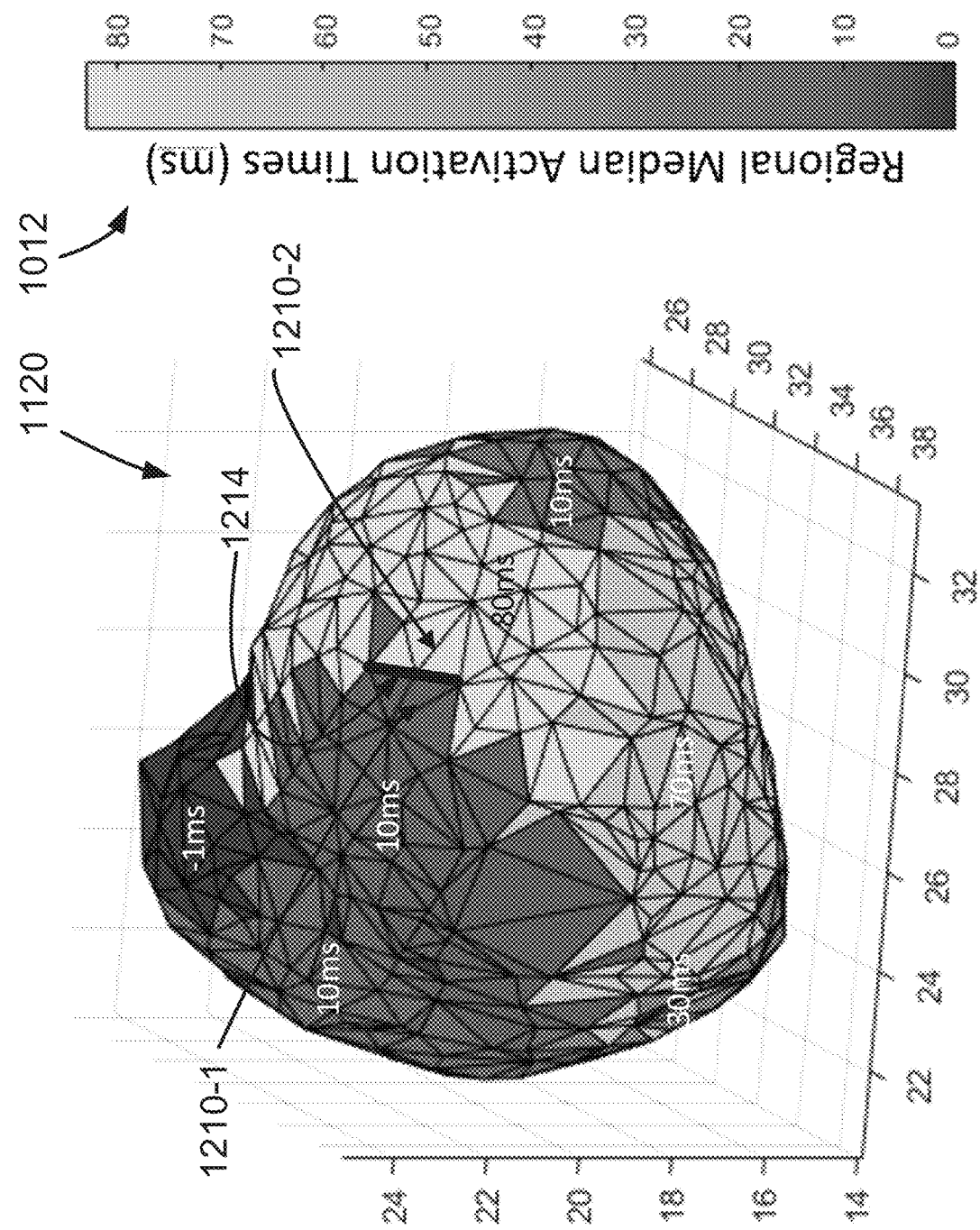
FIG. 9C depicts the model heart of FIG. 9A including conduction condition indicators identifying the conduction conditions.

FIG. 9C depicts the exemplary model heart 1120 illustrating a few conduction conditions indicated by conduction condition indicators. As described in association with FIG. 9B, there can be an electrical activity gradient between two adjacent anatomic regions, such as between first 1210-1 and second 1210-2 anatomic regions. That is, anatomic region 1210-1 has a median activation time corresponding to around ten (10) ms on a regional median activation time indicator 1012 and anatomic region 1210-2, which is adjacent to anatomic region 1210-1, has a median activation time corresponding to around eighty (80) ms. The gradient between the adjacent anatomic regions can indicate a conduction condition. The conduction condition can be visually illustrated by a conduction condition indicator such as a graphical element (e.g., line) 1214 between first 1210-1 and second 1210-2 anatomic regions. While a graphical element is described, any number of elements can be used to indicate the conduction condition, such as an arrow, a displayed letter, etc.

Figure 9D:
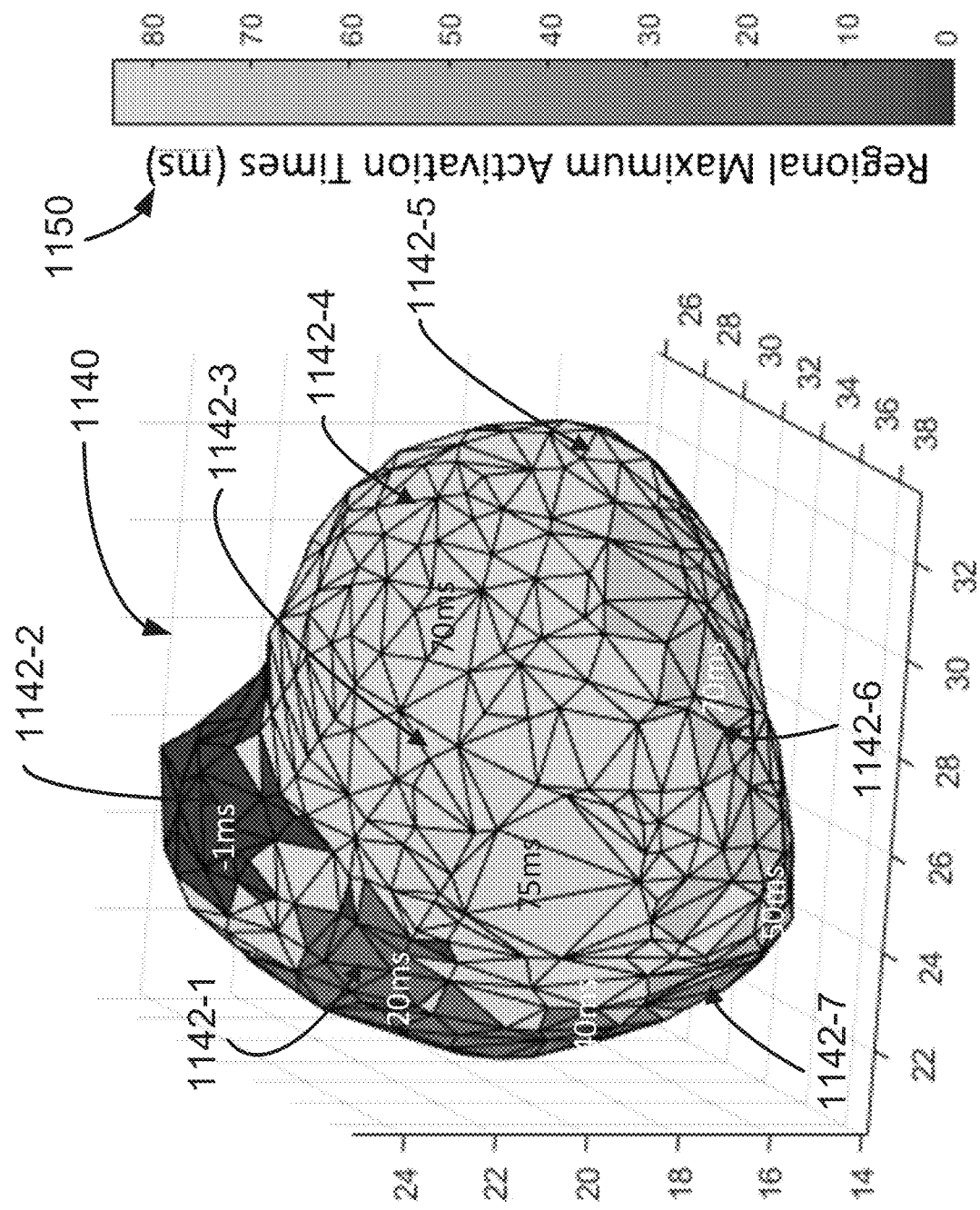
FIG. 9D depicts an exemplary model heart illustrating a plurality of anatomic regions and cardiac electrical activation times mapped thereto.

FIG. 9D depicts an exemplary model heart illustrating a plurality of anatomic regions and cardiac electrical activation times mapped thereto. The model heart 1140 can include a plurality of anatomic regions, a few of which are labeled as 1142-1, 1142-2, 1142-3, 1142-4, 1142-5, 1142-6, 1142-7. The plurality of anatomic regions 1140 are illustrated with a mapping of the electrical activity of each segment illustrated in FIG. 9A being combined across each anatomic region in FIG. 9D. That is, as an example, the electrical activity of segments, illustrated in FIG. 9A, that correspond to an anatomic region can be used to determine a regional maximum activation time for that anatomic region, which is illustrated in FIG. 9D. Put another way, the electrical activity illustrated in FIG. 9A is on a segment-by-segment basis and the maximum of the electrical activity in those segments is illustrated in FIG. 9D for each anatomic region in order to be on a region-by-region basis.

A regional maximum activation time indicator 1150 is illustrated and depicts a color/shade scheme that corresponds with the maximum activation times for each region. That is, anatomic region 1142-1 has a maximum activation time (e.g., the maximum activation time for all the segments within anatomic region 1142-1) corresponding to around twenty (20) ms on the electrical activity indicator 1150. Anatomic region 1142-2 has a maximum activation time corresponding to around negative one (−1) ms on the regional median activation time indicator 1150 which indicates that this anatomical region is not activating myocardium, i.e., not activating valves and vessels. Further, anatomic region 1142-3 has a maximum activation time corresponding to around eighty (80) ms, anatomic region 1142-4 has a maximum activation time corresponding to around eighty (80) ms, and so forth.

Figure 10:
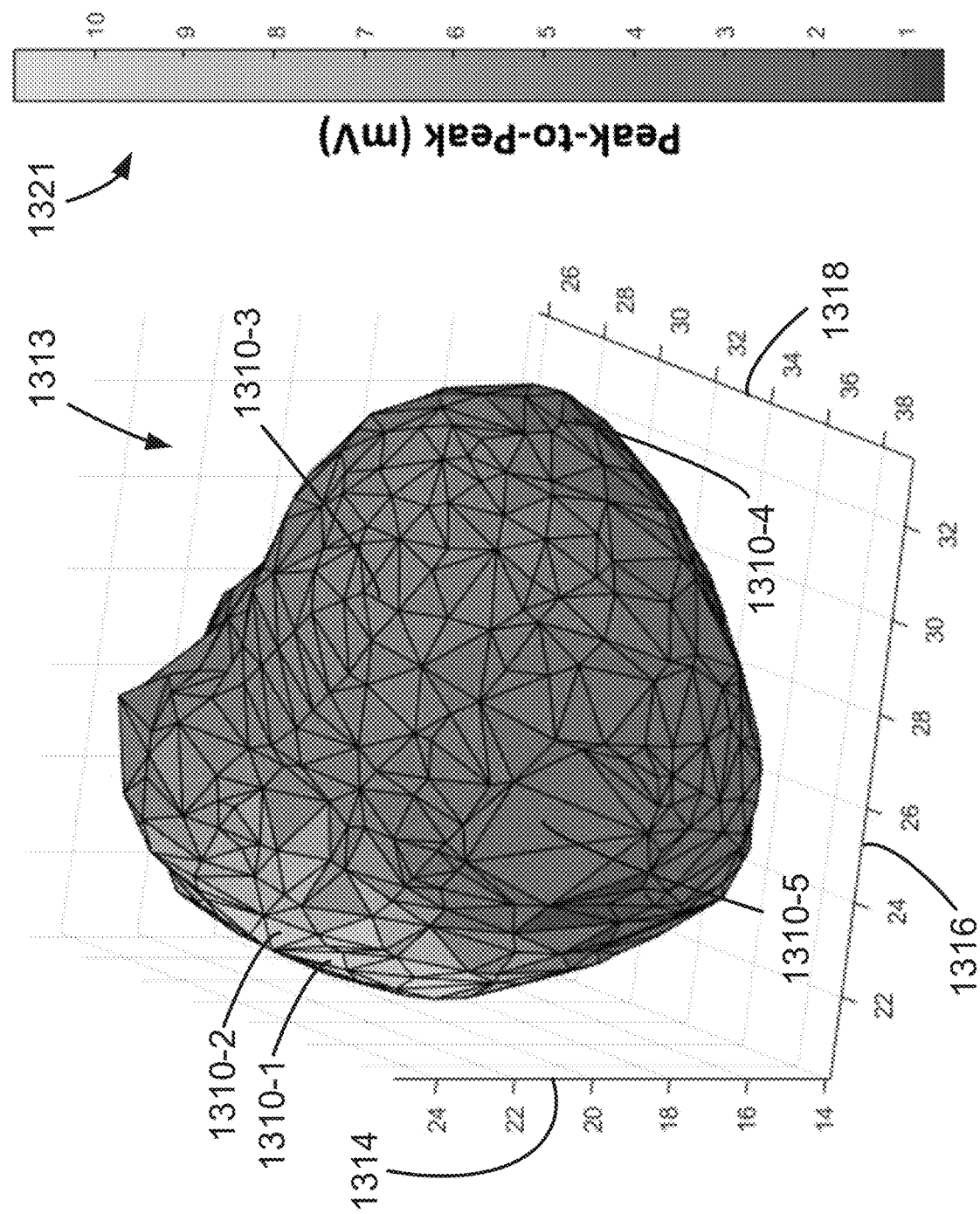
FIG. 10 depicts an exemplary model heart including a plurality of anatomic regions and peak-to-peak values mapped thereto.

FIG. 10 depicts an exemplary model heart 1313 including a plurality of anatomic regions 1310 and peak-to-peak voltage values mapped thereto using the exemplary systems and methods described herein with reference to FIGS. 1-7. Thus, the exemplary model heart 1313 including a plurality of segments 1310 and peak-to-peak voltage values mapped thereto may have been generated, or created, without imaging the patient's heart, and instead, using one or more patient characteristics to provide the model heart 1313 and map the peak-to-peak voltage values thereon. The segments 1310 can each experience a different level or value of peak-to-peak voltage, indicated by a correspondence between the shade/color of the peak-to-peak voltage indicator 1321 and those on the model heart 1313.

Further, as further described herein with reference to process 444, the model heart 1313 can be described as a three-dimensional (3D) representation that extends in the x, y, and z planes, indicated by axes 1316 (x-plane), 1314 (y-plane), and 1318 (z-plane) and as including a plurality of segments, a few of which are labeled as 1310-1, 1310-2, 1310-3, 1310-4, and 1310-5 (referred to herein collectively as 1310).

A first segment 1310-1 is illustrated as having a peak-to-peak voltage value corresponding to around twelve (12) millivolts (mV) on the indicator 1321. A second segment 1310-2 is illustrated as having a peak-to-peak voltage value corresponding to around nine (9) mV on the indicator 1321. A third 1310-3 segment has a peak-to-peak voltage value corresponding to five (5) mV, a fourth 1310-4 corresponding to two (2) mV, and a fifth 1310-5 corresponding to three (3) mV. In this embodiment, each of the mentioned segments can be surrounded by further segments of about the same or very different peak-to-peak voltage values.

While not illustrated in FIG. 10, the peak-to-peak voltages can be averaged and/or combined across an anatomic region, as described in association with FIGS. 9A-9D. In this example, the peak-to-peak voltage values can be an average of peak-to-peak voltages across the anatomic region and not necessarily a particular location within the anatomic region with that value. When traversing away from the mentioned anatomic regions, boundaries extend between anatomic regions of differing peak-to-peak voltages (as described above in association with FIG. 9B and electrical activation times).

Figure 11A:
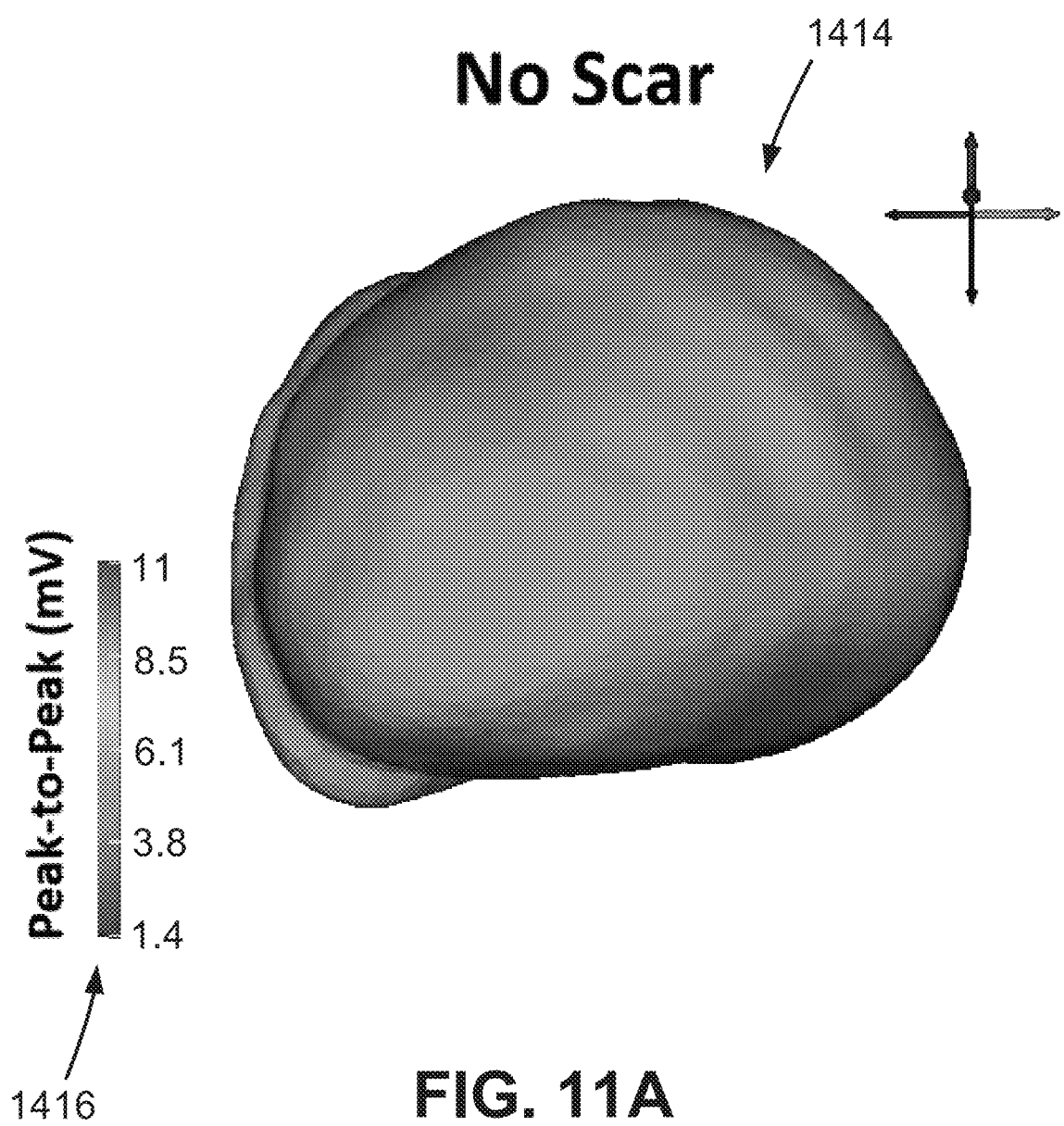
FIG. 11A depicts an exemplary model heart illustrating peak-to-peak voltage values.

FIG. 11A depicts an exemplary model heart illustrating peak-to-peak voltage values. The model heart 1414 illustrates a plurality of peak-to-peak voltage values indicated by the peak-to-peak indicator 1416. The peak-to-peak voltage values of the model heart 1414 are between 3.8 mV and 6.1 mV on the peak-to-peak indicator 1416, approximately near 5 mV. This peak-to-peak voltage value at approximately 5 mV is above a threshold that indicates that there is an absence of scar risk in the model heart tissue.

Figure 11B:
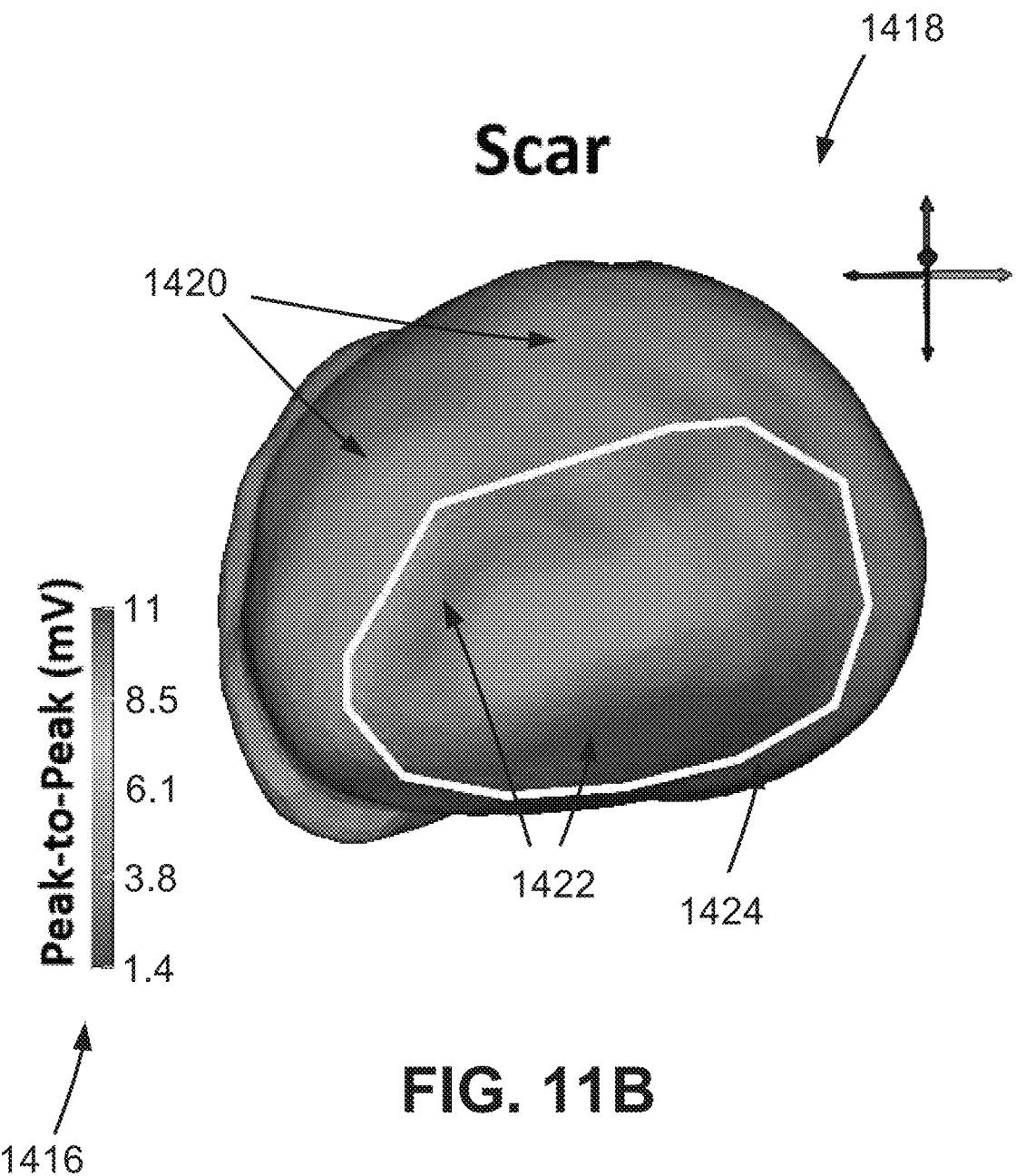
FIG. 11B depicts an exemplary model heart illustrating peak-to-peak voltage values including scar risk indicators identifying increased scar risk.

FIG. 11B depicts an exemplary model heart illustrating peak-to-peak voltage values including scar risk indicators identifying increased scar risk. The model heart 1418 illustrates a plurality of peak-to-peak voltage values indicated by the peak-to-peak indicator 1416. The peak-to-peak voltage values, indicated by arrows 1420, of the model heart 1416 are between 3.8 mV and 6.1 mV on the peak-to-peak indicator 1416, approximately near 5 mV. This peak-to-peak voltage value at approximately 5 mV is above a threshold that indicates that there is an absence of scar risk at these locations in the model heart tissue. However, there are portions 1422 of the model heart 1418 that are below a threshold, at about 1.4 mV on the peak-to-peak indicator 1416. This does indicate a scar risk in the model heart tissue. In response to a portion of the model heart tissue having a peak-to-peak voltage value below a threshold, a scar risk indicator 1424 can be displayed on the model heart 1418.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 12-16.

Figure 12:
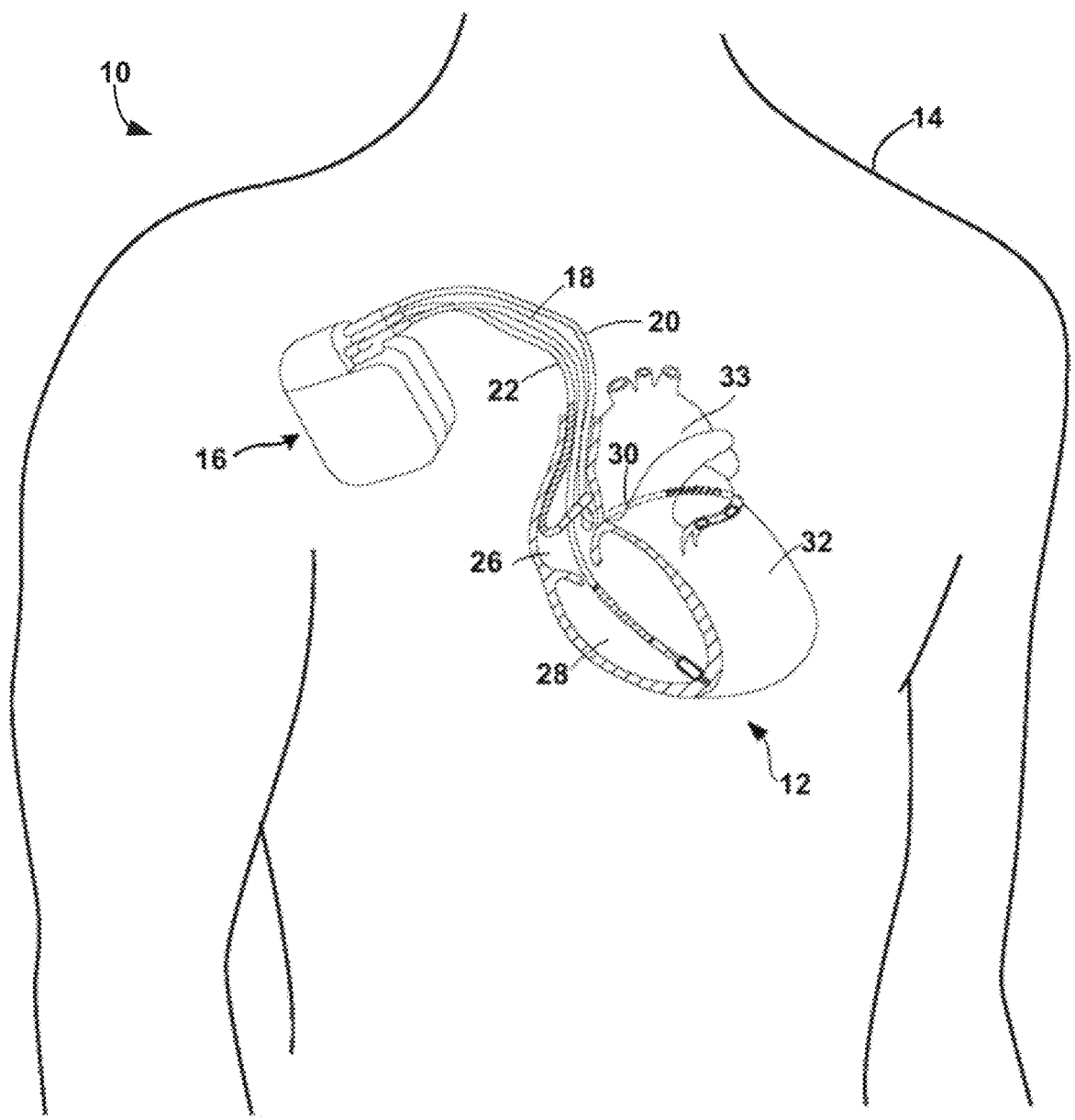
FIG. 12 is a diagram of an exemplary system including an exemplary implantable medical device (IMD).

FIG. 12 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 12, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from.

A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 13:
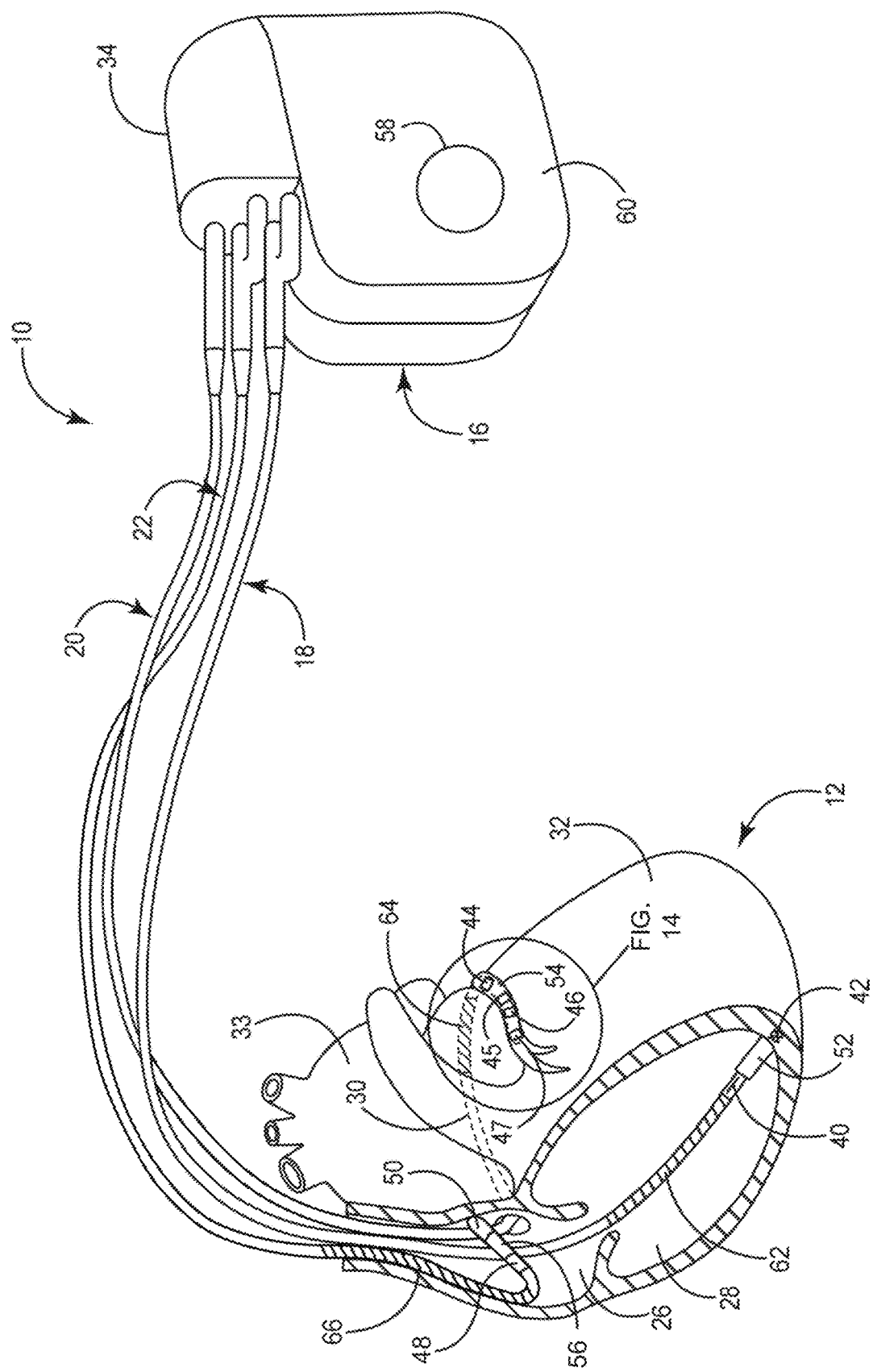
FIG. 13 is a diagram of the exemplary IMD of FIG. 12.
Figure 14:
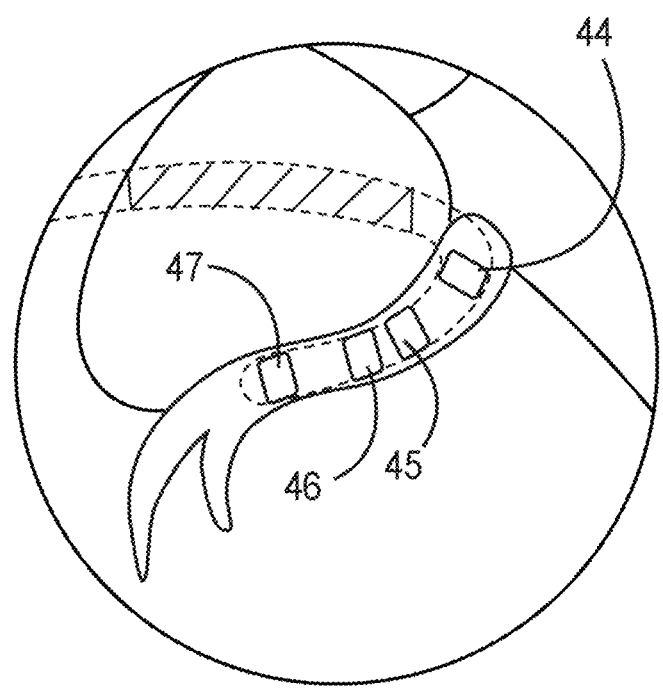
FIG. 14 is a diagram of an enlarged view of a distal end of the electrical lead disposed in the left ventricle of FIG. 13.

FIGS. 13-14 are conceptual diagrams illustrating the IMD 16 and the leads 18, 20, 22 of therapy system 10 of FIG. 12 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance, e.g., of about 21 millimeters (mm), away from electrode 45, electrodes 45 and 46 may be spaced a distance, e.g. of about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 13, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 13, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 12-14 is merely one example. In other examples, the therapy system may include epicardial leads and/or patch electrodes instead of or in addition to the transvenous leads 18, 20, 22 illustrated in FIG. 12. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 12). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 12-14. Still further, other therapy systems may include a single lead that extends from the IMD 16 into the right atrium 26 or the right ventricle 28, or two leads that extend into a respective one of the right atrium 26 and the right ventricle 28.

Figure 15:
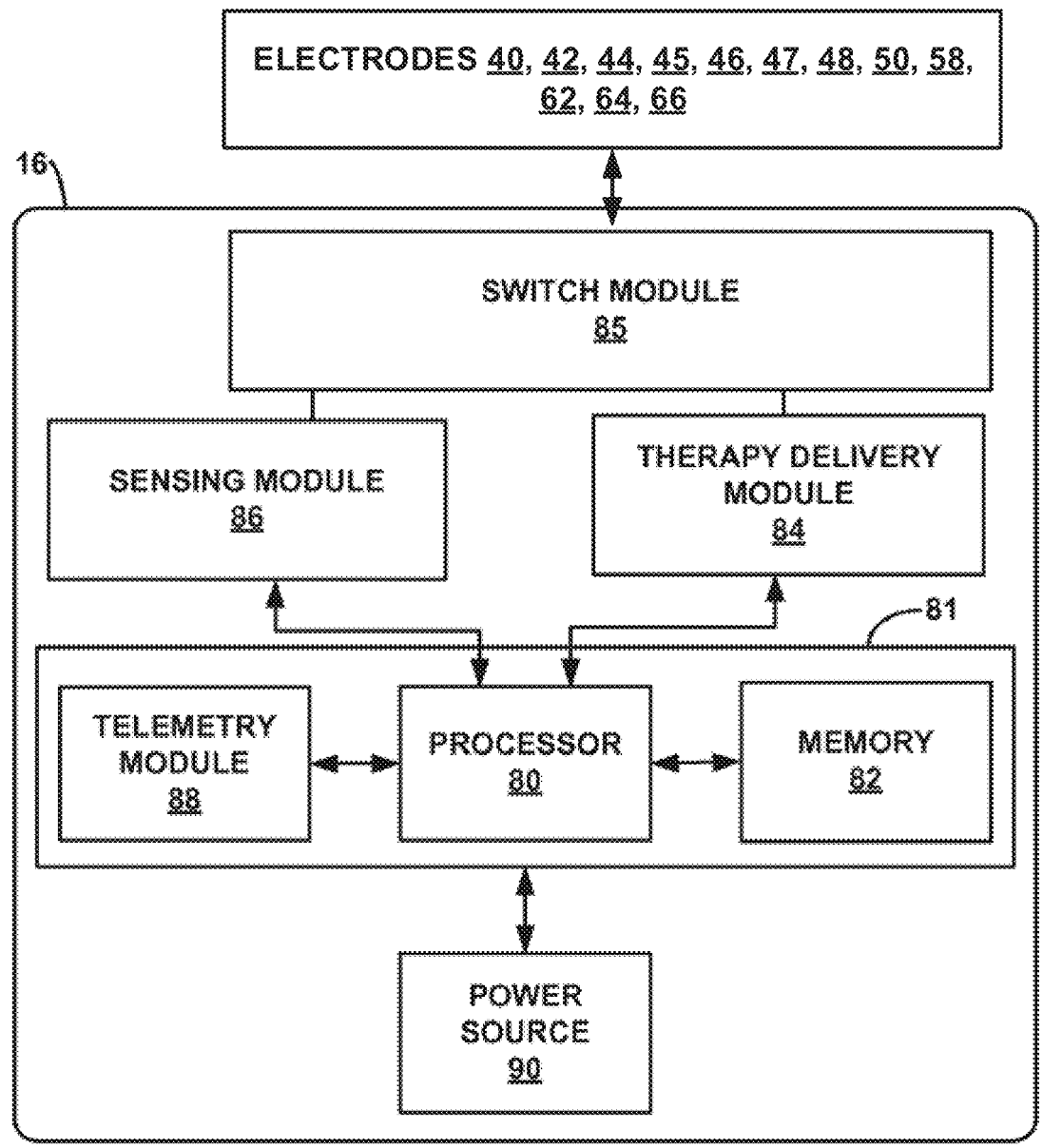
FIG. 15 is a block diagram of an exemplary IMD, e.g., of the systems of FIGS. 12-14.

FIG. 15 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 16:
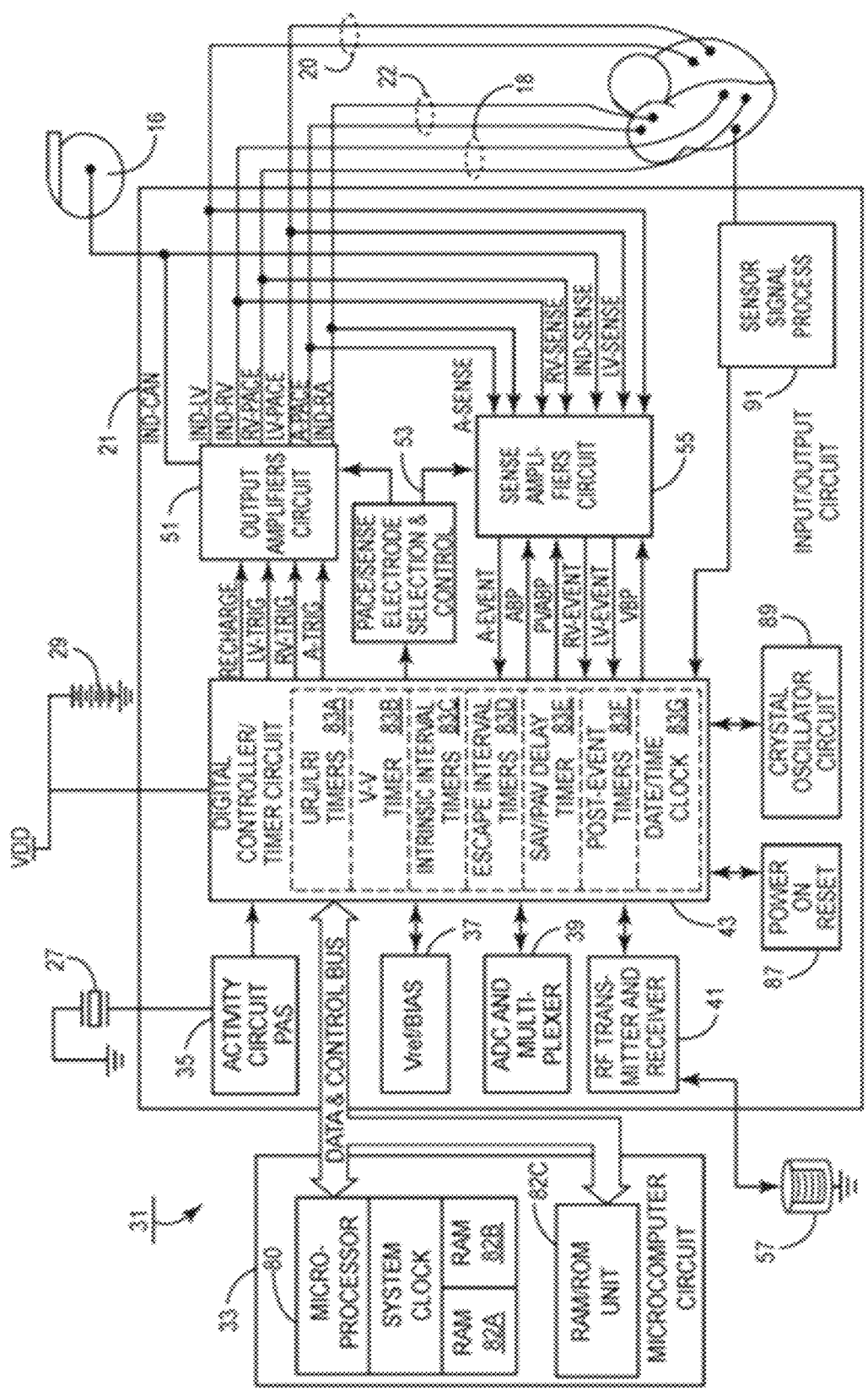
FIG. 16 is another block diagram of an exemplary IMD (e.g., an implantable pulse generator) circuitry and associated leads employed in the systems of FIGS. 12-15.

FIG. 16 is another embodiment of a functional block diagram for IMD 16. FIG. 16 depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

ILLUSTRATIVE EMBODIMENTS

Embodiment 1

A system comprising:
electrode apparatus comprising a plurality of external electrodes to monitor electrical activity from tissue of a patient; and
computing apparatus comprising processing circuitry and coupled to the electrode apparatus and configured to:
monitor electrical activity from the patient using the plurality of external electrodes;
provide a model heart representative of the patient's heart based on at least one of a plurality of patient characteristics, wherein the model heart comprises a plurality of segments;
map the monitored electrical activity onto the plurality of segments of the model heart; and
determine a value of electrical activity for each of a plurality of anatomic regions of the model heart based on the mapped electrical activity, wherein each of the plurality of anatomic regions comprises a subset of the plurality of segments.

Embodiment 2

The system of embodiment 1, wherein providing a model heart representative of the patient's heart based on at least one of a plurality of patient characteristics comprises:
providing a plurality of model hearts; and
selecting the model heart representative of the patient's heart from the plurality of model hearts using the at least one a plurality of patient characteristics.

Embodiment 3

The system of any one of embodiments 1 to 2, wherein providing a model heart representative of the patient's heart based on at least one of a plurality of patient characteristics comprises generating the model heart based on the at least one of the plurality of patient characteristics.

Embodiment 4

The system of any one of embodiments 1 to 3, wherein the plurality of external electrodes comprises surface electrodes positioned in an array configured to be located proximate skin of a torso of the patient.

Embodiment 5

The system of any one of embodiments 1 to 4, wherein the system further comprises a display, wherein the display comprises a graphical user interface configured to assist a user in evaluating patient cardiac health, wherein the computing apparatus is further configured to display the model heart and the mapped electrical activity.

Embodiment 6

The system of any one of embodiments 1 to 5, wherein the plurality of patient characteristics comprise age, gender, height, chest circumference, heart chamber dimensions, ventricular ejection fraction, type of cardiomyopathy, and duration of QRS complex on 12-lead ECG.

Embodiment 7

The system of any one of embodiments 1 to 6, wherein the monitored electrical activity comprises a plurality of torso-surface potential signals, wherein mapping the monitored electrical activity onto the plurality of segments of the model heart comprises:
projecting locations at which the torso-surface potential signals are monitored onto corresponding locations on a model torso;
projecting the torso-surface potential signals onto locations on the model heart based on a geometric relationship between the model heart and the model torso; and
generating a value for each segment of the plurality of segments of the model heart based on the one or more of the plurality of torso-surface potential signals that correspond thereto.

Embodiment 8

The system of any one of embodiments 1 to 7, wherein mapping the monitored electrical activity onto the plurality of anatomic regions of the model heart further comprises calculating metrics of electrical activity from the projected torso-surface potential signals at each location of the segments of the model heart within a corresponding anatomic region.

Embodiment 9

The system of any one of embodiments 1 to 8, wherein the computing apparatus is further configured to:
compare values of adjacent anatomic regions of the plurality of anatomic regions; and
determine slow conduction or conduction block conditions between compared adjacent anatomic regions based on the compared values.

Embodiment 10

The system of embodiment 9, wherein the system further comprises a display, wherein the display comprises a graphical user interface configured to assist a user in evaluating patient cardiac health, wherein the computing apparatus is further configured to display the model heart and the mapped electrical activity,
wherein the computing apparatus is further configured to display a graphical element indicative of a location of the determined slow conduction or conduction block conditions on the model heart.

Embodiment 11

The system of any one of embodiments 1 to 10, wherein mapping the monitored electrical activity onto the plurality of segments of the model heart comprises mapping peak-to-peak voltage values onto the plurality of segments of the model heart.

Embodiment 12

The system of embodiment 11, wherein determining the value of electrical activity for each of the plurality of anatomic regions of the model heart comprises:
determining an indication of scar risk based on the peak-to-peak voltage values being determined for each of the plurality of anatomic regions of the model heart; and
identifying on the model heart the determined indication of scar risk.

Embodiment 13

The system of any one of embodiments 1 to 12, wherein determining the value of electrical activity for each of the plurality of anatomic regions of the model heart comprises determining activation times for each of the plurality of anatomic regions of the model heart.

Embodiment 14

A method comprising:
monitor electrical activity from the patient using a plurality of external electrodes on a torso of a patient;
providing a model heart representative of the patient's heart based on at least one of a plurality of patient characteristics, wherein the model heart comprises a plurality of segments;
mapping the monitored electrical activity onto the plurality of segments of the model heart; and
determining a value of electrical activity for each of a plurality of anatomic regions of the model heart based on the mapped electrical activity, wherein each of the plurality of anatomic regions comprises a subset of the plurality of segments.

Embodiment 15

The method of embodiment 14, wherein providing a model heart representative of the patient's heart based on at least one of a plurality of patient characteristics comprises generating the model heart based on the at least one of the plurality of patient characteristics.

Embodiment 16

The method of any one of embodiments 14 to 15, further comprising displaying the model heart and the mapped electrical activity on a graphical user interface of a display to assist a user in evaluating patient cardiac health.

Embodiment 17

The method of any one of embodiments 14 to 16, wherein the plurality of patient characteristics comprise age, gender, height, chest circumference, heart chamber dimensions, ventricular ejection fraction, type of cardiomyopathy, and duration of QRS complex on clinical 12-lead ECG.

Embodiment 18

The method of any one of embodiments 14 to 17, wherein the monitored electrical activity comprises a plurality of torso-surface potential signals, and wherein mapping the monitored electrical activity onto the plurality of segments of the model heart comprises:
projecting locations at which the torso-surface potential signals are monitored onto corresponding locations on a model torso;
projecting the torso-surface potential signals onto locations on the model heart based on a geometric relationship between the model heart and the model torso;

calculating metrics of electrical activity from the projected torso-surface potential signals at each of the locations of the segments of the model heart; and generating a value for each anatomic region of the plurality of anatomic regions of the model heart based on the one or more of the plurality of torso-surface potential signals that correspond thereto.

Embodiment 19

The method of any one of embodiments 14 to 18, further comprising:

comparing determined values for adjacent anatomic regions of the plurality of anatomic regions; and determining slow conduction or conduction block conditions between compared adjacent anatomic regions based on the compared values.

Embodiment 20

The method of embodiment 19, further comprising:

displaying the model heart, the mapped electrical activity, and the determined values on a graphical user interface of a display to assist a user in evaluating patient cardiac health, and displaying a graphical element indicative of a location of the determined slow conduction or conduction block conditions on the model heart.

Embodiment 21

The method of any one of embodiments 14 to 20, wherein the monitored electrical activity comprises peak-to-peak voltage values and the determined values are peak-to-peak voltage values, and the method further comprises:

determining an indication of scar risk based on the determined peak-to-peak voltage values of each of the plurality of anatomic regions of the model heart; and identifying on the model heart the determined indication of scar risk.

Embodiment 22

A system comprising:

electrode apparatus comprising a plurality of external electrodes to monitor electrical activity from tissue of a patient;

computing apparatus comprising processing circuitry and coupled to the electrode apparatus and configured to:

monitor electrical activity from the patient using the plurality of external electrodes;

provide a model heart representative of the patient's heart based on at least one of a plurality of patient characteristics, wherein the model heart comprises a plurality of anatomic regions;

map the monitored electrical activity onto the plurality of anatomic regions of the model heart; and determine an indication of scar risk based on the monitored electrical activity mapped on the plurality of anatomic regions;

a display, wherein the display comprises a graphical user interface configured to assist a user in evaluating patient cardiac health, wherein the computing apparatus is further configured to display on the display:

the model heart;

the mapped electrical activity; and an identification on the model heart of the determined indication of scar risk.

Embodiment 23

The system of embodiment 22, wherein the computing apparatus is further configured to:

compare monitored electrical activity mapped to adjacent anatomic regions of the plurality of anatomic regions; and determine conduction conditions between compared adjacent anatomic regions based on the compared monitored electrical activity.

Embodiment 24

The system of any one of embodiments 22 to 23, further comprising a display, wherein the display comprises a graphical user interface configured to assist a user in evaluating patient cardiac health, wherein the computing apparatus is further configured to display an indicator of the conduction conditions on the display of the model heart, and the conduction conditions comprises at least one of a conduction block and a risk of scar.

Embodiment 25

The system of any one of embodiments 22 to 24, wherein the computing apparatus is further configured to map activation times onto the plurality of anatomic regions of the model heart.

What is claimed:

1. A system comprising:

a display, wherein the display comprises a graphical user interface configured to assist a user in evaluating patient cardiac health;

electrode apparatus comprising a plurality of external electrodes to monitor electrical activity from tissue of a patient; and computing apparatus comprising processing circuitry and coupled to the electrode apparatus and the display and configured to:

monitor electrical activity from the patient using the plurality of external electrodes;

provide a model heart representative of the patient's heart based on at least one of a plurality of patient characteristics, wherein the model heart comprises a plurality of segments and is divided into a plurality of anatomic regions, wherein each anatomic region of the plurality of anatomic regions comprises two or more segments of the plurality of segments different than the other remaining segments of the plurality of segments, wherein each anatomic region is representative of a region that is less than an entire chamber of the heart;

map the monitored electrical activity onto the plurality of segments of the model heart;

determine a value of electrical activity for each of the plurality of anatomic regions of the model heart based on the mapped electrical activity of the two or more segments corresponding to the anatomic region;

compare values of adjacent anatomic regions of the plurality of anatomic regions;

determine slow conduction or conduction block conditions between compared adjacent anatomic regions based on the compared values;

display, on the graphical user interface, the model heart and the mapped electrical activity on the model heart; and display a graphical element indicative of a location of the determined slow conduction or conduction block conditions on the model heart.

2. The system of claim 1, wherein providing a model heart representative of the patient's heart based on at least one of a plurality of patient characteristics comprises:

providing a plurality of model hearts; and selecting the model heart representative of the patient's heart from the plurality of model hearts using the at least one a plurality of patient characteristics.

3. The system of claim 1, wherein providing a model heart representative of the patient's heart based on at least one of a plurality of patient characteristics comprises generating the model heart based on the at least one of the plurality of patient characteristics.

4. The system of claim 1, wherein the plurality of external electrodes comprises surface electrodes positioned in an array configured to be located proximate skin of a torso of the patient.

5. The system of claim 1, wherein the plurality of patient characteristics comprise age, gender, height, chest circumference, heart chamber dimensions, ventricular ejection fraction, type of cardiomyopathy, and duration of QRS complex on 12-lead ECG.

6. The system of claim 1, wherein the monitored electrical activity comprises a plurality of torso-surface potential signals, wherein mapping the monitored electrical activity onto the plurality of segments of the model heart comprises:

projecting locations at which the torso-surface potential signals are monitored onto corresponding locations on a model torso;

projecting the torso-surface potential signals onto locations on the model heart based on a geometric relationship between the model heart and the model torso; and generating a value for each segment of the plurality of segments of the model heart based on the one or more of the plurality of torso-surface potential signals that correspond thereto.

7. The system of claim 1, wherein mapping the monitored electrical activity onto the plurality of anatomic regions of the model heart further comprises calculating metrics of electrical activity from the projected torso-surface potential signals at each location of the segments of the model heart within a corresponding anatomic region.

8. The system of claim 1, wherein mapping the monitored electrical activity onto the plurality of segments of the model heart comprises mapping peak-to-peak voltage values onto the plurality of segments of the model heart.

9. The system of claim 8, wherein determining the value of electrical activity for each of the plurality of anatomic regions of the model heart comprises:

determining an indication of scar risk based on the peak-to-peak voltage values being determined for each of the plurality of anatomic regions of the model heart; and identifying on the model heart the determined indication of scar risk.

10. The system of claim 1, wherein determining the value of electrical activity for each of the plurality of anatomic regions of the model heart comprises determining activation times for each of the plurality of anatomic regions of the model heart.

11. A method comprising:

monitor electrical activity from the patient using a plurality of external electrodes on a torso of a patient;

providing a model heart representative of the patient's heart based on at least one of a plurality of patient characteristics, wherein the model heart comprises a plurality of segments and is divided into a plurality of anatomic regions, wherein each anatomic region of the plurality of anatomic regions comprises two or more segments of the plurality of segments different than the other remaining segments of the plurality of segments, wherein each anatomic region is representative of a region that is less than an entire chamber of the heart;

mapping the monitored electrical activity onto the plurality of segments of the model heart;

determining a value of electrical activity for each of the plurality of anatomic regions of the model heart based on the mapped electrical activity of the two or more segments corresponding to the anatomic region;

comparing determined values for adjacent anatomic regions of the plurality of anatomic regions;

determining slow conduction or conduction block conditions between compared adjacent anatomic regions based on the compared values;

displaying, on a graphical user interface, the model heart and the mapped electrical activity on the model heart; and displaying a graphical element indicative of a location of the determined slow conduction or conduction block conditions on the model heart.

12. The method of claim 11, wherein providing a model heart representative of the patient's heart based on at least one of a plurality of patient characteristics comprises generating the model heart based on the at least one of the plurality of patient characteristics.

13. The method of claim 11, wherein the plurality of patient characteristics comprise age, gender, height, chest circumference, heart chamber dimensions, ventricular ejection fraction, type of cardiomyopathy, and duration of QRS complex on clinical 12-lead ECG.

14. The method of claim 11, wherein the monitored electrical activity comprises a plurality of torso-surface potential signals, and wherein mapping the monitored electrical activity onto the plurality of segments of the model heart comprises:

projecting locations at which the torso-surface potential signals are monitored onto corresponding locations on a model torso;

projecting the torso-surface potential signals onto locations on the model heart based on a geometric relationship between the model heart and the model torso;

calculating metrics of electrical activity from the projected torso-surface potential signals at each of the locations of the segments of the model heart; and generating a value for each anatomic region of the plurality of anatomic regions of the model heart based on the one or more of the plurality of torso-surface potential signals that correspond thereto.

15. The method of claim 11, wherein the monitored electrical activity comprises peak-to-peak voltage values and the determined values are peak-to-peak voltage values, and the method further comprises:

determining an indication of scar risk based on the determined peak-to-peak voltage values of each of the plurality of anatomic regions of the model heart; and
identifying on the model heart the determined indication of scar risk.

\* \* \* \* \*